(12) United States Patent
Eckelbarger et al.

(10) Patent No.: US 9,006,250 B2
(45) Date of Patent: Apr. 14, 2015

(54) 4-AMINO-6-(HETEROCYCLIC)PICOLINATES AND 6-AMINO-2-(HETEROCYCLIC)PYRIMIDINE-4-CARBOXYLATES AND THEIR USE AS HERBICIDES

(71) Applicant: Dow AgroSciences, LLC, Indianapolis, IN (US)

(72) Inventors: Joseph D. Eckelbarger, Carmel, IN (US); Thomas L. Siddall, Zionsville, IN (US); Norbert M. Satchivi, Carmel, IN (US); Paul R. Schmitzer, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/205,896

(22) Filed: Mar. 12, 2014

(65) Prior Publication Data

US 2014/0274702 A1    Sep. 18, 2014

Related U.S. Application Data

(60) Provisional application No. 61/790,112, filed on Mar. 15, 2013.

(51) Int. Cl.
| | | |
|---|---|---|
| *A01N 43/54* | (2006.01) | |
| *C07D 239/42* | (2006.01) | |
| *C07D 401/04* | (2006.01) | |
| *A01N 43/82* | (2006.01) | |
| *A61K 31/506* | (2006.01) | |
| *C07D 413/04* | (2006.01) | |
| *C07D 417/04* | (2006.01) | |
| *A61K 31/443* | (2006.01) | |

(52) U.S. Cl.
CPC ............... *A01N 43/82* (2013.01); *A61K 31/506* (2013.01); *C07D 413/04* (2013.01); *C07D 417/04* (2013.01); *A61K 31/443* (2013.01)

(58) Field of Classification Search
CPC ... C07D 417/04; A61K 31/443; A61K 31/506
USPC .................. 546/268.4; 544/328; 514/338, 256
See application file for complete search history.

(56) References Cited

U.S. PATENT DOCUMENTS

| | | |
|---|---|---|
| 6,784,137 B2 | 8/2004 | Balko et al. |
| 2003/0114311 A1 | 6/2003 | Balko et al. |
| 2008/0045734 A1 | 2/2008 | Balko et al. |
| 2008/0234262 A1* | 9/2008 | Zask et al. ............... 514/234.2 |
| 2009/0088322 A1 | 4/2009 | Epp et al. |
| 2009/0264429 A1* | 10/2009 | Apodaca et al. .......... 514/235.8 |
| 2010/0137137 A1 | 6/2010 | Rosinger et al. |
| 2010/0179127 A1* | 7/2010 | Floersheim et al. ...... 514/212.08 |
| 2011/0136666 A1 | 6/2011 | Whittingham et al. |
| 2011/0281873 A1* | 11/2011 | Chiang et al. ............. 514/235.8 |
| 2012/0190549 A1 | 7/2012 | Eckelbarger et al. |
| 2012/0295905 A1* | 11/2012 | Witty et al. ................ 514/235.5 |
| 2013/0310358 A1* | 11/2013 | Coats et al. ............... 514/210.2 |
| 2013/0345240 A1* | 12/2013 | Whitten et al. .......... 514/255.05 |

FOREIGN PATENT DOCUMENTS

| | | |
|---|---|---|
| CA | 2842830 | 1/2013 |
| WO | 03/011853 | 2/2003 |
| WO | 2005/063721 | 7/2005 |
| WO | 2007/082076 | 7/2007 |
| WO | 2007/082098 | 7/2007 |
| WO | 2009/023438 | 2/2009 |
| WO | 2009/029735 | 3/2009 |
| WO | 2009/081112 | 7/2009 |
| WO | 2009/138712 | 11/2009 |
| WO | WO 2012149528 A1 * | 11/2012 |
| WO | 2013/014165 | 1/2013 |

OTHER PUBLICATIONS

International Search Report and Written Opinion, dated Jul. 7, 2014, in corresponding International Application No. PCT/US2014/024752, (9 pages).

* cited by examiner

*Primary Examiner* — Alexander R Pagano
(74) *Attorney, Agent, or Firm* — Michael J. Terapane; Meunier Carlin & Curfman, LLC.

(57) ABSTRACT

Novel 4-amino-6-(heterocyclic)picolinic acids and their derivatives and 6-amino-2-(heterocyclic)pyrimidine-4-carboxylates and their derivatives are useful to control undesirable vegetation.

20 Claims, No Drawings

4-AMINO-6-(HETEROCYCLIC)PICOLINATES AND 6-AMINO-2-(HETEROCYCLIC)PYRIMIDINE-4-CARBOXYLATES AND THEIR USE AS HERBICIDES

CROSS REFERENCE TO RELATED APPLICATIONS

This application claims the benefit of U.S. Provisional Application No. 61/790,112 filed on Mar. 15, 2013, which is hereby incorporated herein by reference in its entirety.

FIELD

The invention relates to herbicidal compounds and compositions and to methods for controlling undesirable vegetation.

BACKGROUND

The occurrence of undesirable vegetation, e.g., weeds, is a constant problem facing farmers in crops, pasture, and other settings. Weeds compete with crops and negatively impact crop yield. The use of chemical herbicides is an important tool in controlling undesirable vegetation.

There remains a need for new chemical herbicides that offer a broader spectrum of weed control, selectivity, minimal crop damage, storage stability, ease of handling, higher activity against weeds, and/or a means to address herbicide-tolerance that develops with respect to herbicides currently in use.

SUMMARY OF THE INVENTION

Provided herein are compounds of Formula (I):

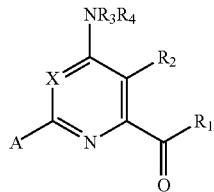

(I)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $-CR^{17}=CR^{18}-SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3''}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy, or $C_1$-$C_6$ alkylamino, or, $R^{3'}$ and $R^{4'}$ taken together with $=C$ represent a 5- or 6-membered saturated ring;

Ar is one of groups Ar1 to Ar4:

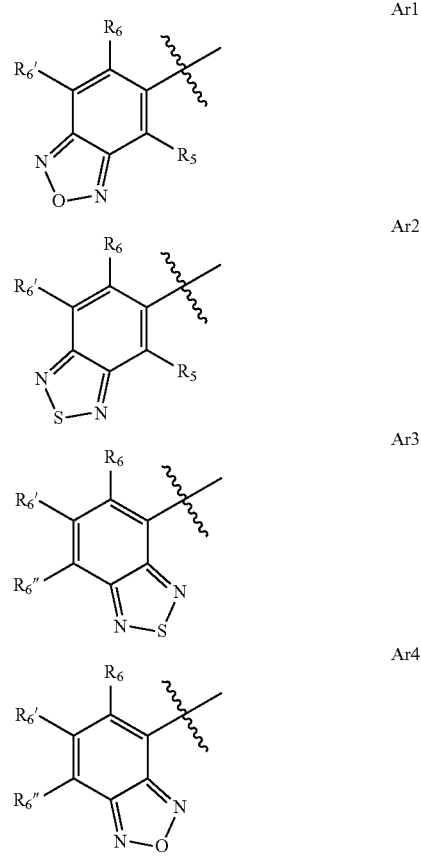

$R^5$, if applicable to the Ar group, is hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, or $C_2$-$C_4$ haloalkylamino, $R^6$ is hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ aminoalkyl or $C_2$-$C_4$ haloaminoalkyl;

$R^{6'}$ is hydrogen or halogen;

$R^{6''}$, if applicable to the Ar group, is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ aminoalkyl or $C_2$-$C_4$ haloaminoalkyl, CN, or $NO_2$;

or an N-oxide or an agriculturally acceptable salt thereof.

Also provided are methods of controlling undesirable vegetation which comprises applying a compound of Formula (I) or an N-oxide or an agriculturally acceptable salt thereof.

DETAILED DESCRIPTION

Definitions

As used herein, herbicide and herbicidal active ingredient mean a compound that controls undesirable vegetation when applied in an appropriate amount.

As used herein, control of or controlling undesirable vegetation means killing or preventing the vegetation, or causing some other adverse modifying effect to the vegetation e.g., deviations from natural growth or development, regulation, desiccation, retardation, and the like.

As used herein, a herbicidally effective or vegetation controlling amount is an amount of herbicidal active ingredient the application of which controls the relevant undesirable vegetation.

As used herein, applying an herbicide or herbicidal composition means delivering it directly to the targeted vegetation or to the locus thereof or to the area where control of undesired vegetation is desired. Methods of application include, but are not limited to pre-emergently contacting soil or water, post-emergently contacting the undesirable vegetation or area adjacent to the undesirable vegetation.

As used herein, plants and vegetation include, but are not limited to, dormant seeds, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can by hydrolyzed, oxidized, metabolized, or otherwise converted, e.g., in plants, water, or soil, to the corresponding carboxylic acid which, depending on the pH, may be in the dissociated or undissociated form.

Suitable salts include those derived from alkali or alkaline earth metals and those derived from ammonia and amines Preferred cations include sodium, potassium, magnesium, and aminium cations of the formula:

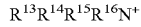

wherein $R^{13}$, $R^{14}$, $R^{15}$ and $R^{16}$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^{13}$, $R^{14}$, $R^{15}$ and $R^{16}$ are sterically compatible. Additionally, any two $R^{13}$, $R^{14}$, $R^{15}$ and $R^{16}$ together may represent an aliphatic difunctional moiety containing one to twelve carbon atoms and up to two oxygen or sulfur atoms. Salts of the compounds of Formula I can be prepared by treatment of compounds of Formula I with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide. Amine salts are often preferred forms of the compounds of Formula I because they are water-soluble and lend themselves to the preparation of desirable aqueous based herbicidal compositions.

Compounds of the formula (I) include N-oxides. Pyridine N-oxides can be obtained by oxidation of the corresponding pyridines. Suitable oxidation methods are described, for example, in Houben-Weyl, Methoden der organischen Chemie [Methods in organic chemistry], expanded and subsequent volumes to the 4th edition, volume E 7b, p. 565 f.

As used herein, unless otherwise specified, acyl refers to formyl, $C_1$-$C_3$ alkylcarbonyl, and $C_1$-$C_3$ haloalkylcarbonyl. $C_1$-$C_6$ acyl refers to formyl, $C_1$-$C_5$ alkylcarbonyl, and $C_1$-$C_5$ haloalkylcarbonyl (the group contains a total of 1 to 6 carbon atoms).

As used herein, alkyl refers to saturated, straight-chained or branched saturated hydrocarbon moieties. Unless otherwise specified, $C_1$-$C_{10}$ alkyl groups are intended. Examples include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl.

As used herein, "haloalkyl" refers to straight-chained or branched alkyl groups, where in these groups the hydrogen atoms may partially or entirely be substituted with halogen atoms. Unless otherwise specified, $C_1$-$C_8$ groups are intended. Examples include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl, and 1,1,1-trifluoroprop-2-yl.

As used herein, alkenyl refers to unsaturated, straight-chained, or branched hydrocarbon moieties containing a double bond. Unless otherwise specified, $C_2$-$C_8$ alkenyl are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. Vinyl refers to a group having the structure —CH=CH$_2$; 1-propenyl refers to a group with the structure —CH=CH—CH$_3$; and 2-propenyl refers to a group with the structure —CH$_2$—CH=CH$_2$.

As used herein, alkynyl represents straight-chained or branched hydrocarbon moieties containing a triple bond. Unless otherwise specified, $C_2$-$C_8$ alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl.

As used herein, alkoxy refers to a group of the formula R—O—, where R is alkyl as defined above. Unless otherwise specified, alkoxy groups wherein R is a $C_1$-$C_8$ alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-prop oxy, 1-ethyl-1-methyl-propoxy, and 1-ethyl-2-methyl-propoxy.

As used herein, haloalkoxy refers to a group of the formula R—O—, where R is haloalkyl as defined above. Unless otherwise specified, haloalkoxy groups wherein R is a $C_1$-$C_8$ alkyl group are intended. Examples include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro, 2-difluoroethoxy, 2,2-dichloro-2-fluoroethoxy, 2,2,2-trichloroethoxy, pentafluoroethoxy, and 1,1,1-trifluoroprop-2-oxy.

As used herein, alkylthio refers to a group of the formula R—S— where R is alkyl as defined above. Unless otherwise specified, alkylthio groups wherein R is a $C_1$-$C_8$ alkyl group are intended. Examples include methylthio, ethylthio, propylthio, 1-methylethylthio, butylthio, 1-methyl-propylthio, 2-methylpropylthio, 1,1-dimethylethylthio, pentylthio, 1-methylbutylthio, 2-methylbutylthio, 3-methylbutylthio, 2,2-dio-methylpropylthio, 1-ethylpropylthio, hexylthio, 1,1-dimethyl propylthio, 1,2-dimethyl propylthio, 1-methylpentylthio, 2-methylpentylthio, 3-methyl-pentylthio, 4-methyl-pentylthio, 1,1-dimethyl butylthio, 1,2-dimethyl-butylthio, 1,3-dimethyl-butylthio, 2,2-dimethyl butylthio, 2,3-dimethyl butylthio, 3,3-dimethylbutylthio, 1-ethylbutylthio, 2-ethylbutylthio, 1,1,2-trimethyl propylthio, 1,2,2-trimethyl propylthio, 1-ethyl-1-methyl propylthio, and 1-ethyl-2-methylpropylthio.

As used herein, haloalkylthio refers to an alkylthio group as defined above wherein the carbon atoms are partially or entirely substituted with halogen atoms. Unless otherwise specified, haloalkylthio groups wherein R is a $C_1$-$C_8$ alkyl group are intended. Examples include chloromethylthio, bromomethylthio, dichloromethylthio, trichloromethylthio, fluoromethylthio, difluoromethylthio, trifluoromethylthio, chlorofluoromethylthio, dichlorofluoro-methylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-difluoroethylthio, 2,2-dichloro-2-fluoroethylthio, 2,2,2-trichloroethylthio, pentafluoroethylthio, and 1,1,1-trifluoroprop-2-ylthio.

As used herein, aryl, as well as derivative terms such as aryloxy, refers to a phenyl, indanyl or naphthyl group with phenyl being preferred. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more substituents selected from halogen, hydroxy, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, $C_1$-$C_6$ alkoxycarbonyl, $C_1$-$C_6$ carbamoyl, hydroxycarbonyl, $C_1$-$C_6$ alkylcarbonyl, aminocarbonyl, $C_1$-$C_6$ alkylaminocarbonyl, $C_1$-$C_6$ dialkylaminocarbonyl, provided that the substituents are sterically compatible and the rules of chemical bonding and strain energy are satisfied. Preferred substituents include halogen, $C_1$-$C_2$ alkyl and $C_1$-$C_2$ haloalkyl.

As used herein alkylcarbonyl refers to an alkyl group bonded to a carbonyl group. $C_1$-$C_3$ alkylcarbonyl and $C_1$-$C_3$ haloalkylcarbonyl refer to groups wherein a $C_1$-$C_3$ alkyl group is bonded to a carbonyl group (the group contains a total of 2 to 4 carbon atoms).

As used herein, alkoxycarbonyl refers to a group of the formula

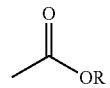

wherein R is alkyl.

As used herein, arylalkyl refers to an alkyl group substituted with an aryl group. $C_7$-$C_{10}$ arylalkyl refers to a group wherein the total number of carbon atoms in the group is 7 to 10.

As used herein alkylamino refers to an amino group substituted with one or two alkyl groups, which may be the same or different.

As used herein haloalkylamino refers to an alkylamino group wherein the alkyl carbon atoms are partially or entirely substituted with halogen atoms.

As used herein, $C_1$-$C_6$ alkylaminocarbonyl refers to a group of the formula RNHC(O)— wherein R is $C_1$-$C_6$ alkyl, and $C_1$-$C_6$ dialkylaminocarbonyl refers to a group of the formula $R_2NC(O)$— wherein each R is independently $C_1$-$C_6$ alkyl.

As used herein alkylcarbamyl refers to a carbamyl group substituted on the nitrogen with an alkyl group.

As used herein alkylsulfonyl refers to a group of the formula

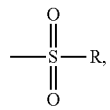

where R is alkyl.

As used herein carbamyl (also referred to as carbamoyl and aminocarbonyl) refers to a group of the formula

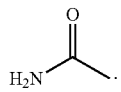

As used herein dialkylphosphonyl refers to a group of the formula

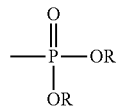

where R is independently alkyl in each occurrence.

As used herein, $C_1$-$C_6$ trialkylsilyl refers to a group of the formula —$SiR_3$ wherein each R is independently a $C_1$-$C_6$ alkyl group (the group contains a total of 3 to 18 carbon atoms).

As used herein Me refers to a methyl group; OMe refers to a methoxy group; i-Pr refers to an isopropyl group.

As used herein, the term "halogen" including derivative terms such as "halo" refers to fluorine, chlorine, bromine and iodine.

As used herein, plants and vegetation include, but are not limited to, germinant seeds, emerging seedlings, plants emerging from vegetative propagules, immature vegetation, and established vegetation.

Compounds of Formula (I)

The invention provides compounds of Formula (I) as defined above and N-oxides and agriculturally acceptable salts thereof.

In some embodiments, the compound is the carboxylic acid or an agriculturally acceptable ester or salt. In some embodiments, the compound is the carboxylic acid or its methyl ester.

In some embodiments, $R^2$ is halogen, $C_2$-$C_4$-alkenyl, $C_2$-$C_4$ haloalkenyl, or $C_1$-$C_4$-alkoxy. In some embodiments, $R^2$ is halogen, $C_2$-$C_4$-alkenyl, or $C_1$-$C_4$ alkoxy. In some embodiments, $R^2$ is Cl, OMe, vinyl, or 1-propenyl. In some embodiments, $R^2$ is Cl. In some embodiments, $R^2$ is OMe. In some embodiments $R^2$ is vinyl or 1-propenyl.

In some embodiments, $R^3$ and $R^4$ are hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, or $R^3$ and $R^4$ taken together represent =$CR^{3'}(R^{4'})$, wherein $R^{3'}$ and $R^{4'}$ are independently hydrogen, $C_1$-$C_6$ alkyl, $C_1$-$C_6$ alkoxy, or $C_1$-$C_6$ alkylamino. In some embodiments, at least one of $R^3$ and $R^4$ are hydrogen. In some embodiments, $R^3$ and $R^4$ are both hydrogen.

In some embodiments, X is N, CH or CF. In some embodiments, X is N. In some embodiments, X is CH. In some embodiments, X is CF.

In some embodiments, Ar is Ar1 or Ar2. In some embodiments Ar is Ar3 or Ar4. In some embodiments Ar is Ar1. In some embodiments Ar is Ar2. In some embodiments Ar is Ar3. In some embodiments Ar is Ar4.

In some embodiments, $R^5$ is hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, or amino. In some embodiments, $R^5$ is hydrogen or halogen. In some embodiments, $R^5$ is hydrogen or F. In some embodiments, $R^5$ is hydrogen. In some embodiments $R^5$ is F.

In some embodiments, $R^6$ is hydrogen, halogen, or amino. In some embodiments, $R^6$ is hydrogen. In some embodiments, $R^6$ is F. In some embodiments, $R^6$ is amino.

In some embodiments, $R^{6'}$ is hydrogen or halogen. In some embodiments, $R^{6'}$ is F or Cl. In some embodiments, $R^{6'}$ is F. In some embodiments, $R^{6'}$ is hydrogen.

In some embodiments, $R^{6''}$ is hydrogen, halogen, $C_1$-$C_4$ alkyl, $C_1$-$C_4$ haloalkyl, cyclopropyl, $C_2$-$C_4$ alkynyl, CN or $NO_2$. In some embodiments $R^{6''}$ is hydrogen or halogen.

In some embodiments:
$R^2$ is halogen, $C_2$-$C_4$-alkenyl, or $C_1$-$C_4$-alkoxy;
$R^3$ and $R^4$ are hydrogen; and
X is N, CH, or CF.

In some embodiments:
$R^2$ is halogen, $C_2$-$C_4$-alkenyl, or $C_1$-$C_4$-alkoxy;
$R^3$ and $R^4$ are hydrogen;
X is N, CH, or CF;
$R^5$, if applicable to the Ar group, is hydrogen or F;
$R^6$ is hydrogen, fluorine, or amino;
$R^{6'}$ is hydrogen;
$R^{6''}$, if applicable to the Ar group, is hydrogen or halogen.

In some embodiments:
$R^2$ is chlorine, vinyl, 1-propenyl, or methoxy;
$R^3$ and $R^4$ are hydrogen; and
X is N, CH, or CF.

In some embodiments:
$R^2$ is chlorine;
$R^3$ and $R^4$ are hydrogen; and
X is N, CH, or CF.

In some embodiments:
$R^2$ is vinyl or 1-propenyl;
$R^3$ and $R^4$ are hydrogen; and
X is N, CH, or CF.

In some embodiments:
$R^2$ is methoxy;
$R^3$ and $R^4$ are hydrogen; and
X is N, CH, or CF.

In some embodiments:
$R^2$ is chlorine, vinyl, 1-propenyl, or methoxy;
$R^3$ and $R^4$ are hydrogen; and
X is N.

In some embodiments:
$R^2$ is chlorine, vinyl, 1-propenyl, or methoxy;
$R^3$ and $R^4$ are hydrogen; and
X is CH.

In some embodiments:
$R^2$ is chlorine, vinyl, 1-propenyl, or methoxy;
$R^3$ and $R^4$ are hydrogen; and
X is CF.

Exemplary Compounds

The following Table 1 describes exemplary compounds of the Formula (I) wherein R is $OR^{1'}$, and $R^3$ and $R^4$ are hydrogen. Table 2 sets forth the structure, appearance, preparation method and precursor(s) used in synthesis of the exemplary compounds. Table 3 sets forth physical data for each of the exemplary compounds.

Blank spaces in Table 1 indicate hydrogen, or that for the Ar group indicated in a particular row, the column in which the blank occurs is not relevant.

TABLE 1

Compounds of Formula (I)

| Compound No. | $R^{1'}$ | $R^2$ | X | A | $R^5$ | $R^6$ | $R^{6'}$ | $R^{6''}$ |
|---|---|---|---|---|---|---|---|---|
| 1 | Me | Cl | CF | Ar1 | | | | |
| 2 | H | Cl | CF | Ar1 | | | | |
| 3 | Me | Cl | CF | Ar1 | | F | | |
| 4 | Me | Cl | CH | Ar1 | | F | | |
| 5 | H | Cl | CH | Ar1 | | | OMe | |
| 6 | Me | Cl | CH | Ar1 | F | | | |
| 7 | H | Cl | CH | Ar1 | | | F | |
| 8 | Me | Cl | CH | Ar1 | | | Cl | |
| 9 | Me | Cl | CH | Ar1 | OMe | | | |
| 10 | Me | OMe | N | Ar1 | | | F | |
| 11 | Me | Cl | CF | Ar2 | | | | |
| 12 | H | Cl | CF | Ar2 | | | | |
| 13 | Me | Cl | CH | Ar2 | | | F | |
| 14 | Me | Cl | CH | Ar2 | F | | | |
| 15 | Me | Cl | CH | Ar4 | | | | Cl |
| 16 | Me | Cl | CH | Ar4 | | | | |
| 17 | Me | Cl | CH | Ar4 | Me | | | |
| 18 | Me | Cl | CH | Ar4 | Cl | | | |

Methods of Preparing the Compounds

Exemplary procedures to synthesize the compounds of Formula (I) are provided below.

The 4-amino-6-(heterocyclic)picolinic acids of Formula (I) can be prepared in a number of ways. As depicted in Scheme I, the 4-amino-6-chloropicolinates of Formula (II) can be converted to the 4-amino-6-substituted-picolinates of Formula (III), wherein Ar is as herein defined, via Suzuki coupling with a boronic acid or ester, in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_1$). 4-Amino-6-substituted-picolinates of Formula (III) can be transformed into the 5-iodo-4-amino-6-substituted-picolinates of Formula (IV) via a reaction with iodinating reagents, such as periodic acid and iodine, in a polar, protic solvent, such as methyl alcohol (reaction $b_1$). Stille coupling of the 5-iodo-4-amino-6-substituted-picolinates of Formula (IV) with a stannane, such as tetramethyltin, in the presence of a catalyst, such as bis(triphenylphosphine)-palladium(II) dichloride, in a non-reactive solvent, such as 1,2-dichloroethane, at a temperature, such as 120-130° C., e.g., in a microwave reactor, provides 5-(substituted)-4-amino-6-substituted-picolinates of Formula (I-A), wherein $Z_1$ is alkyl, alkenyl, alkynyl, haloalkenyl and alkylthio (reaction $c_1$).

Alternatively, 4-amino-6-chloropicolinates of Formula (II) can be transformed to the 5-iodo-4-amino-6-chloropicolinates of Formula (V) via a reaction with iodinating reagents, such as periodic acid and iodine, in a polar, protic solvent, such as methyl alcohol (reaction $b_2$). Stille coupling of the 5-iodo-4-amino-6-chloropicolinates of Formula (V) with a stannane, such as tetramethyltin, in the presence of a catalyst, such as bis(triphenylphosphine)-palladium(II) dichloride, in a non-reactive solvent, such as 1,2-dichloroethane, at a temperature, such as 120-130° C., e.g., in a microwave reactor, provides 5-(substituted)-4-amino-6-chloropicolinates of Formula (VI), wherein $Z_1$ is alkyl, alkenyl, alkynyl, haloalkenyl and alkylthio (reaction $c_2$). The 5-substituted-4-amino-6-chloropicolinates of Formula (VI) can be converted to the 5-substituted-4-amino-6-substituted-picolinates of Formula (I-A), wherein Ar is as herein defined, via Suzuki coupling with a boronic acid or ester, in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_2$).

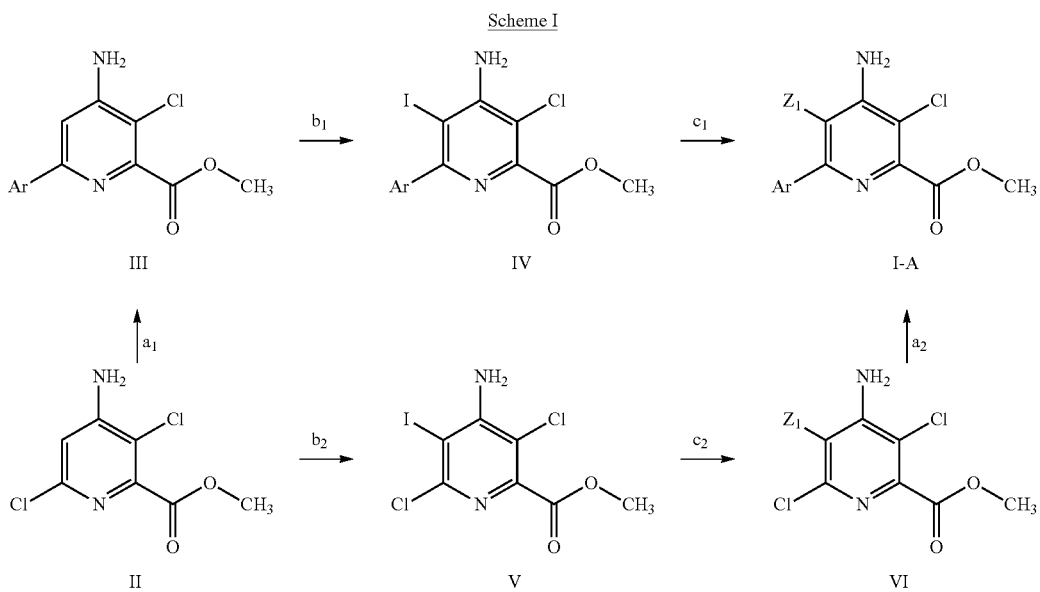

Scheme I

As depicted in Scheme II, the 4,5,6-trichloropicolinate of Formula (VII) can be converted to the corresponding isopropyl ester of Formula (VIII), via a reaction with isopropyl alcohol and concentrated sulfuric acid, e.g., at reflux temperature under Dean-Stark conditions (reaction d). The isopropyl ester of Formula (VIII) can be reacted with a fluoride ion source, such as cesium fluoride, in a polar, aprotic solvent, such as dimethyl sulfoxide (DMSO), at a temperature, such as 80° C., under Dean-Stark conditions, to yield the isopropyl 4,5,6-trifluoropicolinate of Formula (IX) (reaction e). The isopropyl 4,5,6-trifluoropicolinate of Formula (IX) can be aminated with a nitrogen source, such as ammonia, in a polar, aprotic solvent, such as dimethyl sulfoxide, to produce a 4-amino-5,6-difluoropicolinate of Formula (X) (reaction f). The fluoro substituent in the 6-position of the 4-amino-5,6-difluoropicolinate of Formula (X) can be exchanged with a chloro substituent by treatment with a chloride source, such as hydrogen chloride, e.g., in dioxane, in a Parr reactor, at a temperature, such as 100° C., to produce a 4-amino-5-fluoro-6-chloro-picolinate of Formula (XI) (reaction g). The 4-amino-5-fluoro-6-chloro-picolinate of Formula (XI) can be transesterified to the corresponding methyl ester of Formula (XII) by reaction with titanium(IV) isopropoxide in methyl alcohol at reflux temperature (reaction h).

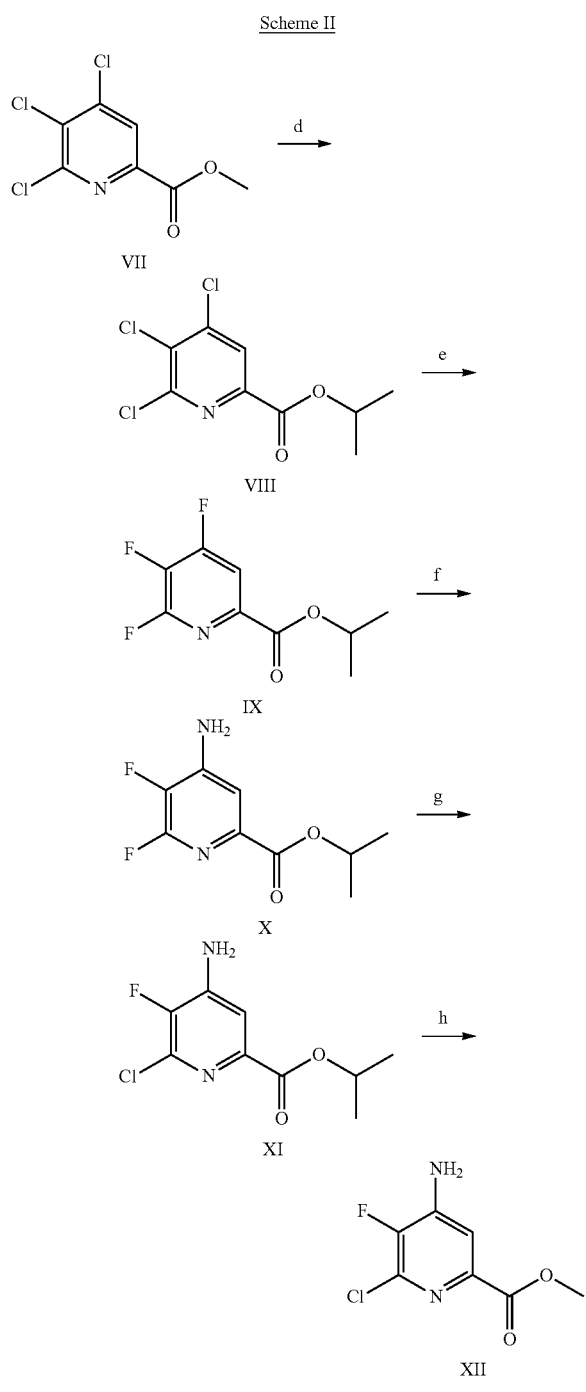

As depicted in Scheme III, the 4-amino-5-fluoro-6-chloropicolinate of Formula (XII) can be transformed into the 3-iodo-4-amino-5-fluoro-6-chloropicolinate of Formula (XIII) via reaction with iodinating reagents, such as periodic acid and iodine, in a polar, protic solvent, such as methyl alcohol (reaction $b_3$). Stille coupling of the 3-iodo-4-amino-5-fluoro-6-chloropicolinates of Formula (XIII) with a stannane, such as tributyl(vinyl)stannane, in the presence of a catalyst, such as bis(triphenylphosphine)-palladium(II) dichloride, in a non-reactive solvent, such as 1,2-dichloroethane, at a temperature, such as 120-130° C., e.g., in a microwave reactor, provides 3-(substituted)-4-amino-5-fluoro-6-chloropicolinates of Formula (XIV), wherein $R^2$ is alkyl, alkenyl, alkynyl, haloalkenyl and alkylthio (reaction $c_3$). Alternatively, the 3-iodo-4-amino-5-fluoro-6-chloropicolinates of Formula (XIII) can be treated with cesium carbonate and a catalytic amount of both copper(I) iodide and 1,10-phenanthroline in the presence of a polar, protic solvent, such as methyl alcohol, at a temperature, such as 65° C., to provide a 3-(substituted)-4-amino-5-fluoro-6-chloropicolinic acids of Formula (XIV), wherein $R^2$ is alkoxy or haloalkoxy (reaction $i_1$), which can be esterified to the methyl esters, e.g., by treatment with hydrogen chloride (gas) and methyl alcohol at 50° C. (reaction $j_1$). The 3-(substituted)-4-amino-5-fluoro-6-chloropicolinates of Formula (XIV) can be converted to the 4-amino-6-substituted-picolinates of Formula (I-B), wherein Ar is as herein defined, via Suzuki coupling with a boronic acid or ester, in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_3$).

Alternatively, the 4-amino-5-fluoro-6-chloropicolinates of Formula (XII) can be converted to the 4-amino-5-fluoro-6-substituted-picolinates of Formula (XV), wherein Ar is as herein defined, via Suzuki coupling with a boronic acid or ester, in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_4$). The 4-amino-5-fluoro-6-substituted-picolinates of Formula (XV) can be transformed into the 3-iodo-4-amino-5-fluoro-6-substituted-picolinates of Formula (XVI) via reaction with iodinating reagents, such as periodic acid and iodine, in a polar, protic solvent, such as methyl alcohol (reaction $b_4$). Stille coupling of the 3-iodo-4-amino-5-fluoro-6-substituted-picolinates of Formula (XVI) with a stannane, such as tributyl(vinyl)stannane, in the presence of a catalyst, such as bis(triphenylphosphine)-palladium (II) dichloride, in a non-reactive solvent, such as 1,2-dichloroethane, at a temperature, such as 120-130° C., e.g., in a microwave reactor, provides 3-(substituted)-4-amino-5-fluoro-6-substituted-picolinates of Formula (I-B), wherein $R^2$ is alkyl, alkenyl, alkynyl, haloalkenyl and alkylthio (reaction $C_4$). Alternatively, the 3-iodo-4-amino-5-fluoro-6-substituted-picolinates of Formula (XVI) can be treated with cesium carbonate and a catalytic amount of both copper(I) iodide and 1,10-phenanthroline in the presence of a polar, protic solvent, such as methyl alcohol, at a temperature, such as 65° C., to provide a 3-(substituted)-4-amino-5-fluoro-6-substituted-picolinic acids of Formula (I-B), wherein $R^2$ is alkoxy or haloalkoxy (reaction $i_2$), which can be esterified to the methyl esters, e.g., by treatment with hydrogen chloride (gas) and methyl alcohol, at a temperature, such as 50° C. (reaction $j_2$).

Scheme III

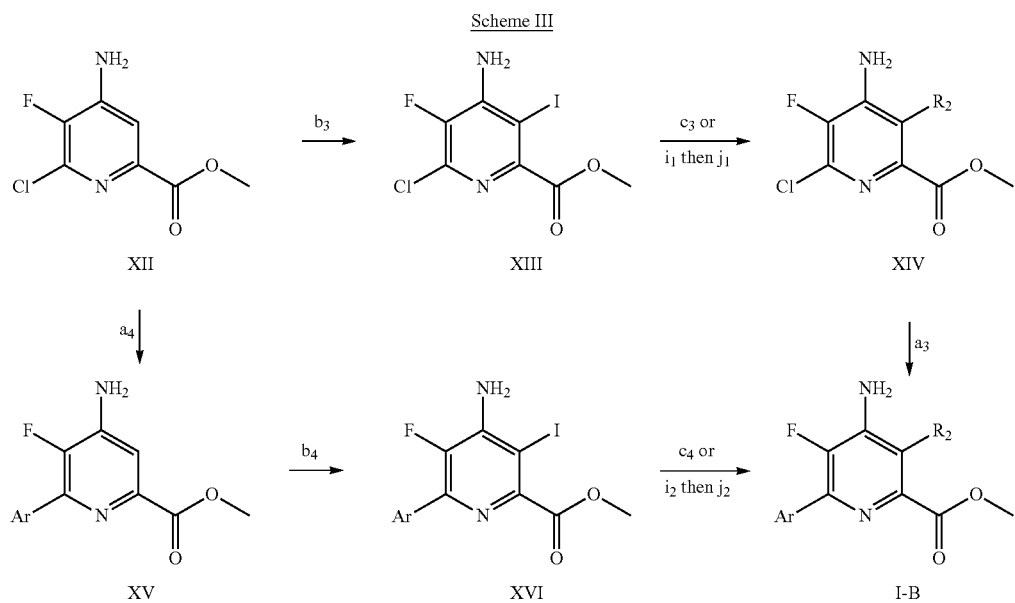

As depicted in Scheme IV, the 4-acetamido-6-(trimethylstannyl)picolinates of Formula (XVII) can be converted to the 4-acetamido-6-substituted-picolinates of Formula (XVIII), wherein Ar is as herein defined, via Stille coupling with an aryl bromide or aryl iodide, in the presence of a catalyst, such as bis(triphenylphosphine)-palladium(II) dichloride, in a solvent, such as dichloroethane, e.g., at reflux temperature (reaction k). 4-Amino-6-substituted-picolinates of Formula (I-C), wherein Ar is as herein defined, can be synthesized from 4-acetamido-6-substituted-picolinates of Formula (XVIII) via standard deprotecting methods, such as hydrochloric acid gas in methanol (reaction l).

Scheme IV

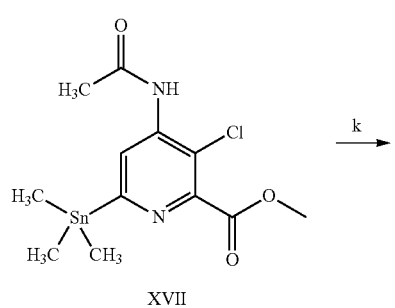

XVII

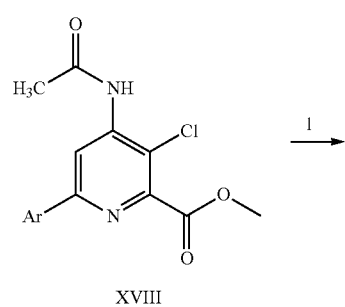

XVIII

-continued

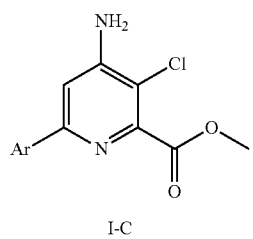

I-C

As depicted in Scheme V, 2,4-dichloro-5-methoxypyrimidine (XIX) can be transformed into 2,4-dichloro-5-methoxy-6-vinylpyrimidine (XX) via a reaction with vinyl magnesium bromide, in a polar, aprotic solvent, such as tetrahydrofuran (reaction m). 2,4-Dichloro-5-methoxy-6-vinylpyrimidine (XX) can be transformed into 2,6-dichloro-5-methoxypyrimidine-4-carboxaldehyde (XXI) via treatment with ozone, e.g., in a dichloromethane:methanol solvent mixture (reaction n). 2,6-Dichloro-5-methoxypyrimidine-4-carboxaldehyde (XXI) can be transformed into methyl 2,6-dichloro-5-methoxypyrimidine-4-carboxylate (XXII) via treatment with bromine, e.g., in a methanol:water solvent mixture (reaction o). Methyl 2,6-dichloro-5-methoxypyrimidine-4-carboxylate (XXII) can be transformed into methyl 6-amino-2-chloro-5-methoxypyrimidine-4-carboxylate (XXIII) via treatment with ammonia (e.g., 2 equivalents) in a solvent, such as DMSO (reaction p). Finally, 6-amino-2-substituted-5-methoxypyrimidine-4-carboxylates of Formula (I-D), wherein Ar is as herein defined, can be prepared via Suzuki coupling with a boronic acid or ester, with 6-amino-2-chloro-5-methoxypyrimidine-4-carboxylate (XXIII), in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_5$).

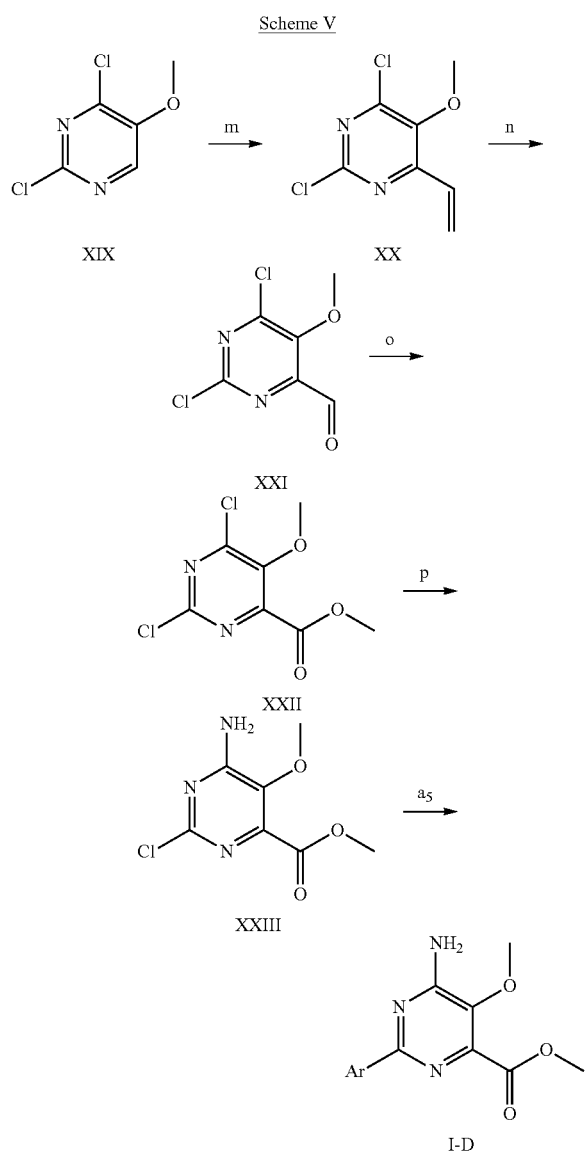

Scheme V

The compounds of Formulae I-A, I-B, I-C, and I-D obtained by any of these processes, can be recovered by conventional means and purified by standard procedures, such as by recrystallization or chromatography. The compounds of Formula (I) can be prepared from compounds of Formulae I-A, I-B, I-C, and I-D using standard methods well known in the art.

Compositions and Methods

In some embodiments, the compounds provided herein are employed in mixtures containing an herbicidally effective amount of the compound along with at least one agriculturally acceptable adjuvant or carrier. Exemplary adjuvants or carriers include those that are not phytotoxic or significantly phytotoxic to valuable crops, e.g., at the concentrations employed in applying the compositions for selective weed control in the presence of crops, and/or do not react or significantly react chemically with the compounds provided herein or other composition ingredients. Such mixtures can be designed for application directly to weeds or their locus or can be concentrates or formulations that are diluted with additional carriers and adjuvants before application. They can be solids, such as, for example, dusts, granules, water dispersible granules, or wettable powders, or liquids, such as, and for example, emulsifiable concentrates, solutions, emulsions or suspensions. They can also be provided as a pre-mix or tank-mixed.

Suitable agricultural adjuvants and carriers that are useful in preparing the herbicidal mixtures of the disclosure are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethylhexyl stearate, n-butyl oleate, isopropyl myristate, propylene glycol dioleate, di-octyl succinate, di-butyl adipate, di-octyl phthalate and the like; esters of mono-, di- and poly-carboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers, and the like. In some embodiments, water is the carrier for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

In some embodiments, one or more surface-active agents are utilized in the compositions of the present disclosure. Such surface-active agents are, in some embodiments, employed in both solid and liquid compositions, e.g., those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in *McCutcheon's Detergents and Emulsifiers Annual*, MC Publishing Corp., Ridgewood, N.J., 1998, and in *Encyclopedia of Surfactants*, Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono- and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, e.g., methyl esters.

Oftentimes, some of these materials, such as vegetable or seed oils and their esters, can be used interchangeably as an agricultural adjuvant, as a liquid carrier or as a surface active agent.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this disclosure is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation or flood water, and by other conventional means known to those skilled in the art.

In some embodiments, the compounds and compositions described herein are applied as a post-emergence application, pre-emergence application, in-water application to flooded paddy rice or water bodies (e.g., ponds, lakes and streams), or burn-down application.

In some embodiments, the compounds and compositions provided herein are utilized to control weeds in crops, including but not limited to citrus, apple, rubber, oil, palm, forestry, direct-seeded, water-seeded and transplanted rice, wheat, barley, oats, rye, sorghum, corn/maize, pastures, grasslands, rangelands, fallowland, turf, tree and vine orchards, aquatics, or row-crops, as well as non-crop settings, e.g., industrial vegetation management (IVM) or rights of way. In some embodiments, the compounds and compositions are used to control woody plants, broadleaf and grass weeds, or sedges.

In some embodiments, the compounds and compositions provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (fall panicum, PANDI), *Paspalum dilatatum* Poir. (dallisgrass, PASDI), *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SCPJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (monochoria, MOOKA), *Monochoria vaginalis* (Burm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/ Rydb. Ex Hill (hemp sesbania, SEBEX), or *Sphenoclea zeylanica* Gaertn. (gooseweed, SPDZE).

In some embodiments, the compounds and compositions provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POAAN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Mum (field violet, VIOAR), or *Viola tricolor* L. (wild violet, VIOTR).

In some embodiments, the compounds and compostions provided herein are utilized to control undesirable vegetation in range and pasture. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA),

*Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the compounds and compositions provided herein are utilized to control undesirable vegetation found in row crops. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common pursuance, POROL), *Sida spinosa* L. (prickly sida, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

In some embodiments, application rates of about 1 to about 4,000 grams/hectare (g/ha) are employed in post-emergence operations. In some embodiments, rates of about 1 to about 4,000 g/ha are employed in pre-emergence operations.

In some embodiments, the compounds, compositions, and methods provided herein are used in conjunction with one or more other herbicides to control a wider variety of undesirable vegetation. When used in conjunction with other herbicides, the presently claimed compounds can be formulated with the other herbicide or herbicides, tank-mixed with the other herbicide or herbicides or applied sequentially with the other herbicide or herbicides. Some of the herbicides that can be employed in conjunction with the compounds of the present disclosure include: 4-CPA; 4-CPB; 4-CPP; 2,4-D; 2,4-D choline salt, 2,4-D esters and amines; 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-ammonium, glyphosate, halosafen, halosulfuron-methyl, haloxydine, haloxyfop-methyl, haloxyfop-P-methyl, halauxifen-methyl, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-methyl, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr esters and amines, tridiphane, trietazine, trifloxysulfuron, trifluralin, triflusulfuron, trifop, trifopsime, trihydroxytriazine, trimeturon, tripropindan, tritac, tritosulfuron, vernolate and xylachlor.

The compounds and compositions of the present disclosure can generally be employed in combination with known herbicide safeners, such as benoxacor, benthiocarb, brassinolide, cloquintocet (e.g., mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, MG 191, MON 4660, naphthalic anhydride (NA), oxabetrinil, R29148 and N-phenylsulfonylbenzoic acid amides, to enhance their selectivity.

The compounds, compositions, and methods described herein be used to control undesirable vegetation on glyphosate-tolerant-, glufosinate-tolerant-, dicamba-tolerant-, phenoxy auxin-tolerant-, pyridyloxy auxin-tolerant-, aryloxyphenoxypropionate-tolerant-, acetyl CoA carboxylase (ACCase) inhibitor-tolerant-, imidazolinone-tolerant-, acetolactate synthase (ALS) inhibitor-tolerant-, 4-hydroxyphenyl-pyruvate dioxygenase (HPPD) inhibitor-tolerant-, protoporphyrinogen oxidase (PPO) inhibitor-tolerant-, triazine-tolerant-, bromoxynil-tolerant-crops (such as, but not limited to, soybean, cotton, canola/oilseed rape, rice, cereals, corn, turf, etc), for example, in conjunction with glyphosate, glufosinate, dicamba, phenoxy auxins, pyridyloxy auxins, aryloxyphenoxypropionates, ACCase inhibitors, imidazolinones, ALS inhibitors, HPPD inhibitors, PPO inhibitors, triazines, and bromoxynil. The compositions and methods may be used in controlling undesirable vegetation in crops possessing multiple or stacked traits conferring tolerance to multiple chemistries and/or inhibitors of multiple modes of action.

The compounds and compositions provided herein may also be employed to control herbicide resistant or tolerant weeds. Exemplary resistant or tolerant weeds include, but are not limited to, biotypes resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes-of-action.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

SYNTHESIS OF PRECURSORS

Preparation 1: Methyl 4-amino-3,6-dichloropicolinate (Head A)

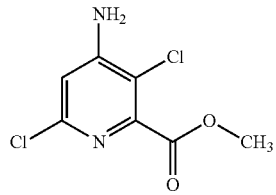

Prepared as described in Fields et al., WO 2001051468 A1.

Preparation 2: Methyl 4-amino-3,6-dichloro-5-fluoropicolinate (Head B)

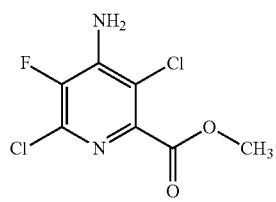

Prepared as described in Fields et al., *Tetrahedron Letters* (2010), 51(1), 79-81.

Preparation 3: 2,6-Dichloro-5-methoxy-4-vinyl pyrimidine

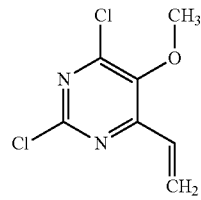

To a solution of commercially available 2,6-dichloro-5-methoxy pyrimidine (100 grams (g), 0.55 moles (mol)) in dry tetrahydrofuran (THF) was added, dropwise, 1 molar (M) vinyl magnesium bromide in tetrahydrofuran solvent (124 g, 0.94 mol) over one hour (h) at room temperature. The mixture was then stirred for 4 h at room temperature. Excess Grignard reagent was quenched by addition of acetone (200 milliliters (mL)) while the temperature of the mixture was maintained at a temperature below 20° C. Thereafter, 2,3-dichloro-5,6-dicyano-p-benzoquinone (DDQ) (151 g, 0.67 mol) was added at once and stirred overnight. A yellow solid precipitated out. The solid was filtered and washed with ethyl acetate (500 mL). The filtrate was concentrated under reduced pressure and the resulting crude compound was diluted with ethyl acetate (2 liters (L)). The resulting undissolved, dark, semi-solid was separated by filtration using ethyl acetate. It was further concentrated under reduced pressure to provide a crude compound, which was purified by column chromatography. The compound was eluted with 5% to 10% ethyl acetate in hexane mixture to provide the title compound (70 g, 60%): mp 60-61° C.; $^1$H NMR (CDCl$_3$) δ 3.99 (s, 3H), 5.85 (d, 1H), 6.75 (d, 1H), 6.95 (dd, 1H).

Preparation 4: 2,6-Dichloro-5-methoxy-pyrimidine-4-carbaldehyde

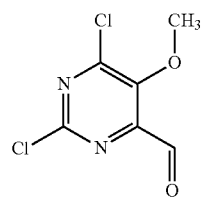

A solution of 2,6-dichloro-5-methoxy-4-vinyl pyrimidine (50 g, 0.24 mol) in dichloromethane:methanol (4:1, 2 L) was cooled to −78° C. Ozone gas was bubbled therethrough for 5 h. The reaction was quenched with dimethyl sulfide (50 mL). The mixture was slowly warmed to room temperature and concentrated under reduced pressure at 40° C. to provide the title compound (50.5 g, 100%); high-performance liquid chromatography (HPLC) (85% acetonitrile buffered with 0.1% volume per volume (v/v) acetic acid).

Preparation 5: Methyl 2,6-dichloro-5-methoxy-pyrimidine-4-carboxylate

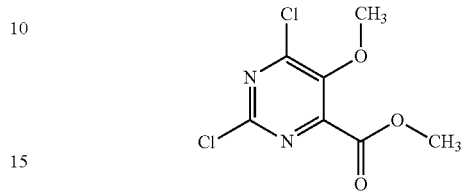

A solution of 2,6-dichloro-5-methoxy-pyrimidine-4-carbaldehyde (50 g, 0.24 mol) in methanol (1 L) and water (60 mL) was prepared. To the solution, sodium bicarbonate (400 g) was added. A 2 M solution of bromine (192 g, 1.2 mol) in methanol/water (600 mL, 9:1) was added, dropwise, to the pyrimidine solution for 45 minutes (min) at 0° C. while stirring the mixture. The stirring was continued at the same temperature for 1 h. Later, the mixture was stirred at room temperature for 4 h. While stirring, the reaction mixture was thereafter poured onto a mixture of crushed ice (2 L), sodium bisulfate (50 g), and sodium chloride (200 g). The product was extracted with ethyl acetate (1 L×2), and the combined organic layer was dried over sodium sulfate and filtered. Evaporation of the solvent under reduced pressure produced a thick material, which solidified on long standing to afford the title compound (50.8 g, 87%); ESIMS m/z 238 ([M+H]$^+$).

Preparation 6: Methyl 6-amino-2-chloro-5-methoxy-pyrimidine-4-carboxylate (Head C)

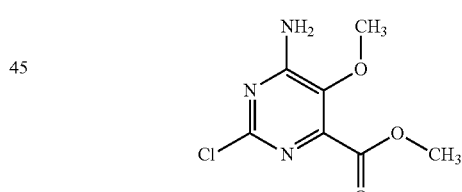

A solution of methyl 2,6-dichloro-5-methoxy-pyrimidine-4-carboxylate (25 g, 0.1 mol) and dimethyl sulfoxide (DMSO) was prepared. To this solution was added, at 0-5° C., a solution of ammonia (2 eq) in DMSO. This mixture was stirred at the same 0-5° C. temperature for 10 to 15 min. Later, the mixture was diluted with ethyl acetate, and the resulting solid was filtered off. The ethyl acetate filtrate was washed with a brine solution and dried over sodium sulfate. Upon concentration, the crude product was obtained. The crude product was stirred in a minimum amount of ethyl acetate and filtered to obtain the pure compound. Additional pure compound was obtained from the filtrate which, after concentration, was purified by flash chromatography. This produced the title compound (11 g, 50%): mp 158° C.; $^1$H NMR (DMSO-d$_6$) δ 3.71 (s, 3H), 3.86 (s, 3H), 7.65 (brs, 1H), 8.01 (brs, 1H).

Preparation 7: Methyl 4-amino-3,6-dichloro-5-iodopicolinate

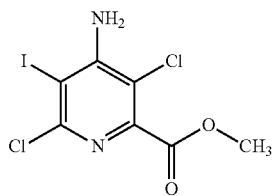

Methyl 4-amino-3,6-dichloropicolinate (10.0 g, 45.2 millimoles (mmol)), periodic acid (3.93 g, 17.2 mmol), and iodine (11.44 g, 45.1 mmol) were dissolved in methanol (30 mL) and refluxed at 60° C. for 27 h. The reaction mixture was concentrated, diluted with diethyl ether, and washed twice with saturated aqueous sodium bisulfite. The aqueous layers were extracted once with diethyl ether, and the combined organic layers were dried over anhydrous sodium sulfate. The product was concentrated and purified by flash chromatography (silica gel, 0-50% ethyl acetate/hexanes) to provide the title compound as a pale yellow solid (12.44 g, 35.9 mmol, 79%): mp 130.0-131.5° C.; $^1$H NMR (400 MHz, CDCl$_3$) δ 5.56 (s, 2H), 3.97 (s, 3H); $^{13}$C NMR (101 MHz, CDCl$_3$) δ 163.80, 153.00, 152.75, 145.63, 112.12, 83.91, 53.21; EIMS m/z 346.

Preparation 8: Methyl 4-amino-3,6-dichloro-5-methylpicolinate (Head D)

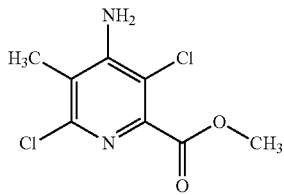

A mixture of methyl 4-amino-3,6-dichloro-5-iodopicolinate (8.1 g, 23.4 mmol), tetramethylstannane (8.35 g, 46.7 mmol), and bis(triphenylphosphine)palladium(II) chloride (2.5 g, 3.5 mmol) in 1,2-dichloroethane (40 mL) was irradiated in a Biotage Initiator microwave at 120° C. for 30 min, with external infrared (IR)-sensor temperature monitoring from the side. The reaction mixture was loaded directly onto a silica gel cartridge and purified by flash chromatography (silica gel, 0-50% ethyl acetate/hexanes) to provide the title compound as an orange solid (4.53 g, 19.27 mmol, 83%): mp 133-136° C.; $^1$H NMR (400 MHz, CDCl$_3$) δ 4.92 (s, 2H), 3.96 (s, 3H), 2.29 (s, 3H); $^{13}$C NMR (101 MHz, CDCl$_3$) δ 164.34, 150.24, 148.69, 143.94, 117.01, 114.60, 53.02, 14.40; ESIMS m/z 236 ([M+H]$^+$), 234 ([M−H]$^-$).

Preparation 9: Methyl 6-amino-2,5-dichloropyrimidine-4-carboxylate (Head E)

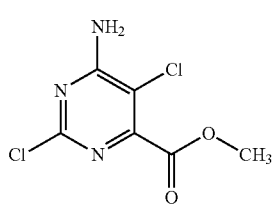

Prepared as described in Epp et al., WO 2007082076 A1.

Preparation 18: Methyl 4-amino-6-chloro-5-fluoro-3-methoxypicolinate (Head F)

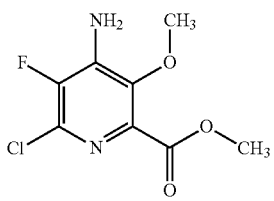

Prepared as described in Epp et al., WO 2013003740 A1.

Preparation 19: Methyl 4-amino-6-chloro-5-fluoro-3-vinylpicolinate (Head G)

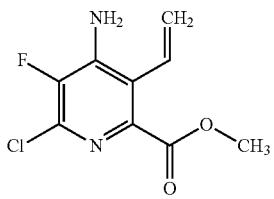

Methyl 4-amino-6-chloro-5-fluoro-3-iodopicolinate (7.05 g, 21.33 mmol, prepared as described in Epp et al., WO 2013003740 A1) and vinyltri-n-butyltin (7.52 mL, 25.6 mmol) were suspended in dichloroethane (71.1 mL) and the mixture was degassed with Argon for 10 min. bis(triphenylphosphine)palladium(II) chloride (1.497 g, 2.133 mmol) was then added and the reaction mixture was stirred at 70° C. overnight (clear orange solution). The reaction was monitored by gas chromatography-mass spectrometry (GCMS). After 20 h, the reaction mixture was concentrated, adsorbed onto Celite, and purified by column chromatography (SiO2, hexanes/ethyl acetate gradient) to afford the title compound as a light brown solid (3.23 g, 65.7%) as a light brown solid: mp 99-100° C.; $^1$ H NMR (400 MHz, CDCl$_3$) δ 6.87 (dd, J=18.1, 11.6 Hz, 1H), 5.72 (dd, J=11.5, 1.3 Hz, 1H), 5.52 (dd, J=18.2, 1.3 Hz, 1H), 4.79 (s, 2H), 3.91 (s, 3H); $^{19}$F NMR (376 MHz, CDCl$_3$) δ −138.79 (s); EIMS m/z 230.

Preparation 20: Methyl 4-amino-3,5,6-trichloropicolinate (Head H)

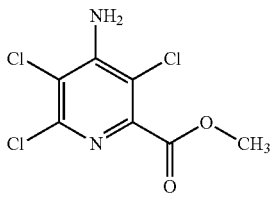

Prepared as described in Finkelstein et al., WO 2006062979 A1.

Preparation 21: Methyl 4-amino-6-bromo-3-chloro-5-fluoropicolinate (Head I)

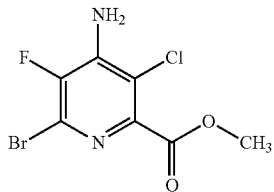

Prepared as described in Arndt et al., US 20120190857 A1.

Preparation 22: Methyl 4-amino-3-chloro-5-fluoro-6-(trimethylstannyl)picolinate (Head J)

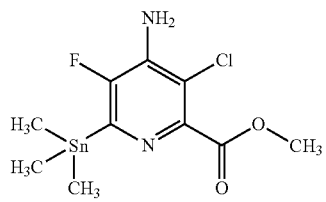

Methyl 4-amino-6-bromo-3-chloro-5-fluoropicolinate (500 mg, 1.8 mmol), 1,1,1,2,2,2-hexamethyldistannane (580 mg, 1.8 mmol) and bis(triphenylphosphine)-palladium(II) chloride (120 mg, 0.18 mmol) were combined in 6 mL dry dioxane, sparged with a stream of nitrogen for 10 min and then heated to 80° C. for 2 h. The cooled mixture was stirred with 25 mL ethyl acetate and 25 mL saturated NaCl for 15 min. The organic phase was separated, filtered through diatomaceous earth, dried ($Na_2SO_4$) and evaporated. The residue was taken up in 4 mL ethyl acetate, stirred and treated in portions with 15 mL hexane. The milky white solution was decanted from any solids produced, filtered through glass wool and evaporated to give the title compound as an off-white solid (660 mg, 100%): $^1$H NMR (400 MHz, $CDCl_3$) δ 4.63 (d, J=29.1 Hz, 1H), 3.97 (s, 2H), 0.39 (s, 4H); $^{19}$F NMR (376 MHz, $CDCl_3$) δ −130.28; EIMS m/z 366.

Preparation 23: Methyl 4-acetamido-3-chloro-6-(trimethylstannyl)-picolinate (Head K)

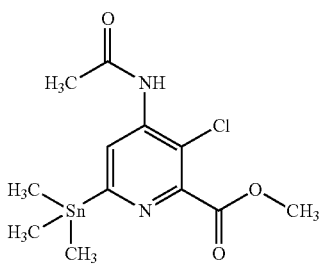

Prepared as described in Balko et al., WO 2003011853 A1.

Preparation 24: Methyl 4-acetamido-3,6-dichloropicolinate (Head L)

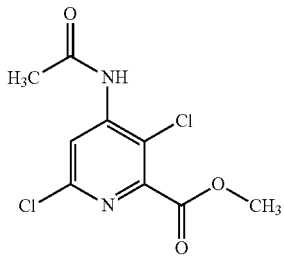 [SMILES: COC(=O)c1nc(Cl)cc(NC(C)=O)c1Cl]

Prepared as described in Fields et al., WO 2001051468 A1.

Preparation 25: Methyl 4-amino-3-chloro-6-iodopicolinate (Head M)

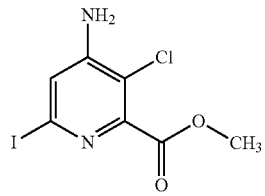

Prepared as described in Balko et al., WO 2007082098 A2.

Preparation 26: Methyl 4-acetamido-3-chloro-6-iodopicolinate (Head N)

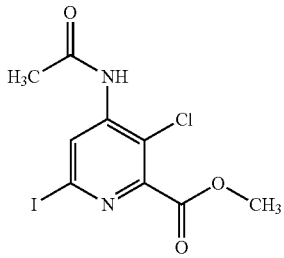 [SMILES: COC(=O)c1nc(I)cc(NC(C)=O)c1Cl]

Prepared as described in Balko et al., WO 2007082098 A2.

Preparation 27: Methyl 4-amino-6-bromo-3,5-difluoropicolinate (Head O)

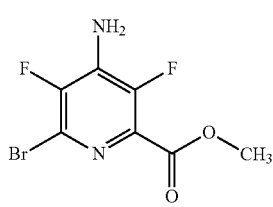

Prepared as described in Fields et al., WO 2001051468 A1.

Preparation 28: Methyl 6-amino-2-chloro-5-vinylpyrimidine-4-carboxylate (Head P)

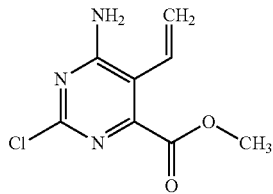

Prepared as described in Epp et al., US20090088322.

Preparation 29: 5-Bromo-6-fluorobenzo[c][1,2,5]oxadiazole 1-oxide

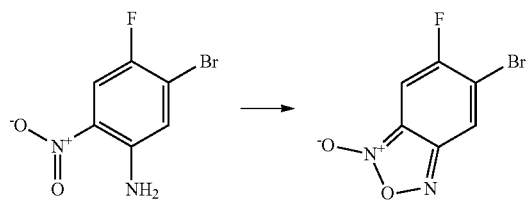

4-Bromo-5-fluoro-2-nitroaniline (8.5 g, 36 mmol) was stirred in 200 mL ethanol and treated with 45% KOH solution (4.5 g, 36 mmol) to produce a dark solution. This solution was cooled to 0-5° C. and treated dropwise with 6% NaOCl solution (84 g, 68 mmol) over 20 min while maintaining the temperature below 10° C. After 90 min, the mixture was diluted with 300 mL water and extracted twice with 200 mL portions of ethyl acetate. The combined extracts were washed with 30 mL saturated NaCl, dried (Na$_2$SO$_4$) and evaporated. The crude material was chromatographed on silica gel with a 0-30% ethyl acetate-hexane gradient to give the title compound as pale yellow solid (3.5 g, 42%): mp 87-89° C.; $^1$H NMR (400 MHz, CDCl$_3$) δ 7.82 (s, 1H), 7.23 (s, 1H); $^{19}$F NMR (376 MHz, CDCl$_3$) δ −96.03; EIMS m/z 232.

Preparation 30: 5-Bromo-6-fluorobenzo[c][1,2,5]oxadiazole

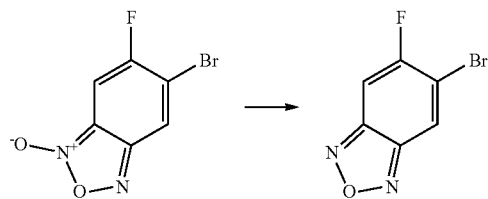

6-bromo-5-fluorobenzo[c][1,2,5]oxadiazole 1-oxide (3.2 g, 14 mmol) was stirred in 30 mL ethanol, treated with triethylphosphite (3.4 g, 21 mmol) and heated to 45° C. After 90 min, the mixture was cooled and the volatiles were removed by rotary evaporation. The crude product was chromatographed on silica gel with a 0-10% ethyl acetate-hexane gradient to give the title compound as tan crystals (2.2 g, 73%): mp 59-61° C.; $^1$H NMR (400 MHz, CDCl$_3$) δ 8.23 (dt, J=2.8, 1.4 Hz, 1H), 7.53 (m, 1H); $^{19}$F NMR (376 MHz, CDCl$_3$) δ −96.99; EIMS m/z 216.

Preparation 31: 6-Bromo-7-fluorobenzo[c][1,2,5]oxadiazole 1-oxide

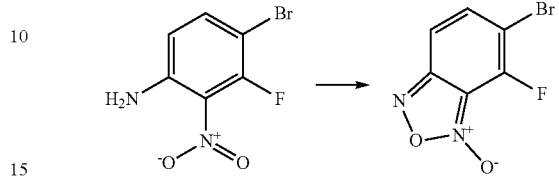

4-Bromo-3-fluoro-2-nitroaniline (1.5 g, 6.4 mmol) was added to cooled (0-5° C.) solution of sodium hydroxide (96 ml, 2 M, 190 mmol) in 80 mL t-butanol. After stirring for 10 min, 5% sodium hypochlorite solution (46 g, 31 mmol) was added dropwise over 10 min. After stirring for 1 h at 0-5° C., the mixture was extracted twice with 100 mL portions of dichloromethane. The combined extracts were washed with 50 mL saturated NaCl, dried (Na$_2$SO$_4$) and evaporated. The material was purified by silica gel chromatography using a 0-20% ethyl acetate-hexane gradient to give 1.4 g of the title compound as red oil that crystallized on standing (1.4 g, 94%): $^1$H NMR (400 MHz, CDCl$_3$) δ 7.26 (q, J=5.9 Hz, 1H), 7.14 (d, J=9.2 Hz, 1H); $^{19}$F NMR (376 MHz, CDCl$_3$) δ −117.47; EIMS m/z 232.

Preparation 32: 5-Bromo-4-fluorobenzo[c][1,2,5]oxadiazole

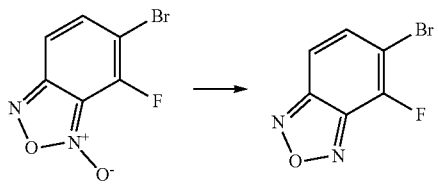 [SMILES: [O-][n+]1onc2ccc(Br)c(F)c21 ; Fc1c(Br)ccc2nonc12]

6-Bromo-7-fluorobenzo[c][1,2,5]oxadiazole 1-oxide (1.2 g, 5.0 mmol) was added to neat trimethyl phosphite (6.2 g, 50 mmol) and heated to 95° C. for 2 h. After cooling the solution was deposited on silica gel and chromatographed with a 0-10% ethyl acetate-hexane gradient to give the partially purified product which was further purified by Kugelrohr distillation to give the title compound as low melting, white crystals (460 mg, 43%): $^1$H NMR (400 MHz, CDCl$_3$) δ 7.61 (m, 1H), 7.51 (dd, J=9.4, 5.6 Hz, 1H); $^{19}$F NMR (376 MHz, CDCl$_3$) δ −111.68; EIMS m/z 216.

Preparation 33: 5-Bromo-4-chlorobenzo[c][1,2,5]oxadiazole 1-oxide

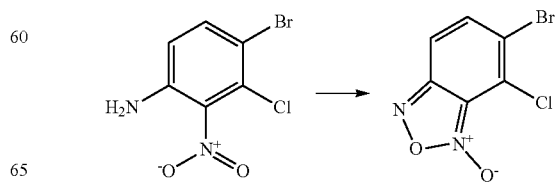

4-Bromo-3-chloro-2-nitroaniline (4.1 g, 16 mmol) was dissolved in 60 mL ethanol, treated with 45% potassium hydroxide solution (2.0 g, 16 mmol), cooled to −5 to 0° C. and treated drop wise with commercial bleach solution (32 mL, 6 wt. %, 31 mmol) over 20 min. The mixture was stirred for 90 min at 0-15° C. and poured into 700 mL water. The precipitated product was collected by filtration, washed well with water and then dried under vacuum at 80° C. to give the title compound (3.2 g, 81%): EIMS m/z 248.

Preparation 34:
5-Bromo-4-chlorobenzo[c][1,2,5]oxadiazole

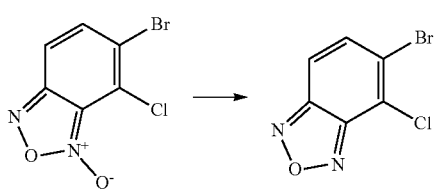 [SMILES: [O-][n+]1onc2ccc(Br)c(Cl)c21 ; Clc1c(Br)ccc2nonc12]

The crude 5-bromo-4-chlorobenzo[c][1,2,5]oxadiazole 1-oxide (3.2 g, 12.8 mmol) was stirred in 50 ml ethanol, treated with triethyl phosphite (3.2 g, 19 mmol) and heated to reflux for 5 h. After cooling, the volatiles were removed by rotary evaporation, the residue was taken up in 75 mL dichloromethane and stirred with 20 mL bleach solution for 20 min. The organic phase was washed with 10 mL saturated NaCl, dried ($Na_2SO_4$) and evaporated. The crude material was purified by flash chromatography on silica to give the title compound as an orange solid (1.5 g, 50%): mp 96-97° C.; $^1$H NMR (400 MHz, CDCl$_3$) δ 7.68 (d, J=9.4 Hz, 1H), 7.59 (d, J=9.3 Hz, 1H); EIMS m/z 232.

Preparation 35:
4-Bromo-7-chlorobenzo[c][1,2,5]oxadiazole

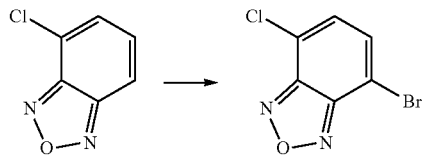 [SMILES: Clc1cccc2nonc12 ; Clc1ccc(Br)c2nonc12]

4-Chlorobenzo[c][1,2,5]oxadiazole (1.0 g, 6.5 mmol) was treated with iron powder (14 mg, 0.2 mmol), stirred and heated to 50° C. and then treated in portions with bromine (1.1 g, 7.1 mmol) to produce a homogeneous red melt solution. The flask was fitted with a reflux condenser and the temperature was raised to 85° C. and stirred for 60 min. An additional 450 mg of bromine were added, heating was continued for 1 h more and then the mixture was allowed to stand for 18 h at 20° C. The solid contents of the flask were dissolved in 15 mL dichloromethane and stirred for 30 min with 15 mL saturated $Na_2SO_3$ solution. The mixture was diluted with 30 mL ethyl acetate and the organic phase was washed with 15 mL saturated NaCl, dried ($Na_2SO_4$) and concentrated under vacuum. The material was chromatographed on silica with a 0-7% ethyl acetate-hexane gradient to give the title compound as a white solid (1.4 g; 93%): mp 81-83° C.; $^1$H NMR (400 MHz, CDCl$_3$) δ 7.58 (d, J=7.5 Hz, 1H), 7.33 (d, J=7.5 Hz, 1H); EIMS m/z 232.

Preparation 36:
6-Bromo-5-chlorobenzo[c][1,2,5]oxadiazole 1-oxide

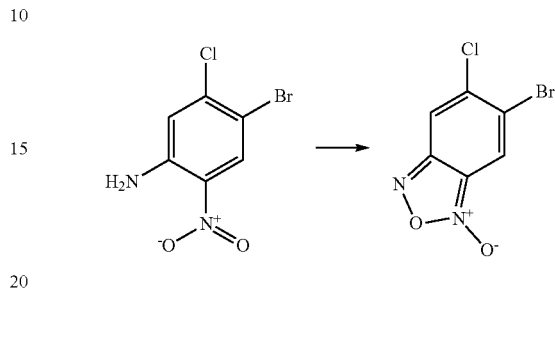

4-Bromo-5-chloro-2-nitroaniline (13.3 g, 53 mmol) was dissolved in 250 mL ethanol, treated with potassium hydroxide (10 g, 88%, 160 mmol) and heated at 60° C. for 2 h. The mixture was cooled to 0-5° C. and treated with dropwise with commercial bleach solution (320 g, 5%, 210 mmol). The cooling was removed and the mixture was stirred for 2 h at 20° C. The mixture was diluted with 1.5 liter of water and the precipitated product was collected by filtration and washed well with water. The wet product was taken up in 250 mL ethyl acetate, washed twice with 50 mL water, 50 mL saturated NaCl, dried ($Na_2SO_4$) and evaporated. The residue was chromatographed on silica with a 0-40% ethyl acetate-hexane gradient to give the title compound (5.0 g, 38%): mp 123-125° C. $^1$H NMR (400 MHz, CDCl$_3$) δ 7.91 (s, 1H), 7.68 (s, 1H); EIMS m/z 248.

Preparation 37:
5-Bromo-6-chlorobenzo[c][1,2,5]oxadiazole

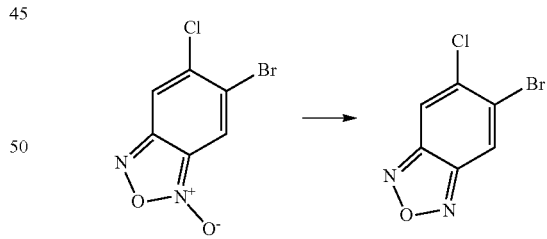

6-Bromo-5-chlorobenzo[c][1,2,5]oxadiazole 1-oxide (4.8 g, 19 mmol) was taken up 150 ml ethanol, heated to reflux, treated with triethyl phosphite (8.8 g, 53 mmol) and heated for 3.5 h. After cooling, the volatiles were removed by rotary evaporation, the residue was taken up in 100 mL dichloromethane and stirred with 50 mL bleach solution for 30 min. The organic phase was washed with 20 mL saturated NaCl, dried ($Na_2SO_4$) and evaporated. The crude material was purified by flash chromatography with a 0-30% ethyl acetate-hexane gradient to give the title compound as an orange solid (3.5 g, 79%): mp 68-69° C.; $^1$H NMR (400 MHz, CDCl$_3$) δ 8.30 (s, 1H), 8.05 (s, 1H); EIMS m/z 232.

Preparation 38:
5-Bromo-6-fluorobenzo[c][1,2,5]thiadiazole

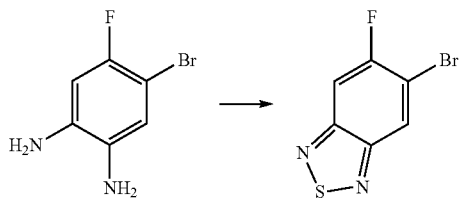 [SMILES: Nc1cc(F)c(Br)cc1N ; Fc1cc2nsnc2cc1Br]

4-Bromo-5-fluorobenzene-1,2-diamine (500 mg, 2.4 mmol) was dissolved in 20 mL chloroform, treated in portions with thionyl chloride (580 mg, 4.9 mmol) and heated to reflux for 20 h. After cooling the mixture was diluted with 60 mL ethyl acetate, washed with 15 mL water, 15 mL saturated NaCl, dried (Na$_2$SO$_4$) and concentrated under vacuum. The material was chromatographed on silica with a 0-30% ethyl acetate-hexane gradient to give the title compound as a white solid (425 mg, 76%): mp 79-82° C.; $^1$H NMR (400 MHz, CDCl$_3$) δ 8.33 (d, J=6.7 Hz, 1H), 7.72 (d, J=8.3 Hz, 1H); $^{19}$F NMR (376 MHz, CDCl$_3$) δ −102.91; EIMS m/z 232.

Preparation 39:
5-Bromo-4-fluorobenzo[c][1,2,5]thiadiazole

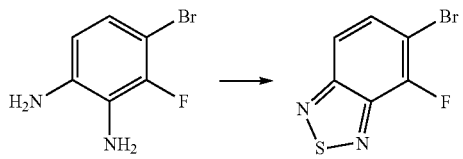 [SMILES: Nc1ccc(Br)c(F)c1N ; Fc1c(Br)ccc2nsnc12]

5-Bromo-4-fluorobenzo[c][1,2,5]thiadiazole was prepared as described in Preparation 38 from 4-bromo-3-fluorobenzene-1,2-diamine: $^1$H NMR (400 MHz, CDCl$_3$) δ 7.72 (m, 1H); $^{19}$F NMR (376 MHz, CDCl$_3$) δ −111.82; EIMS m/z 232.

Preparation 40: 4-Bromo-3-methyl-2-nitroaniline

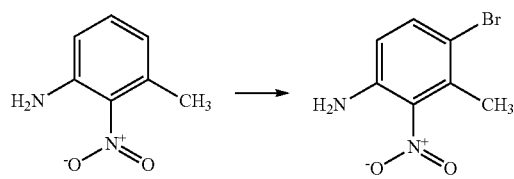

3-methyl-2-nitroaniline (6.2 g, 41 mmol) was dissolved in 150 mL acetic acid, stirred and treated in portions with N-bromosuccinimide (7.3 g, 41 mmol). After 1 h the mixture was poured into 400 mL water with stirring. The precipitated product was collected by filtration, washed well with water, and then taken up in 200 mL ethyl acetate. This solution was washed with 50 mL water, 50 mL saturated NaHCO$_3$, 50 mL saturated NaCl, dried (Na$_2$SO$_4$) and evaporated under vacuum to give the title compound as a bright orange solid (8.2 g, 87%): $^1$H NMR (400 MHz, CDCl$_3$) δ 7.44-7.33 (d, J=8.8 Hz, 1H), 6.62-6.49 (d, J=8.8 Hz, 1H), 4.75 (s, 2H), 2.41 (s, 3H); EIMS m/z 230.

Preparation 41:
6-Bromo-7-methylbenzo[c][1,2,5]oxadiazole 1-oxide

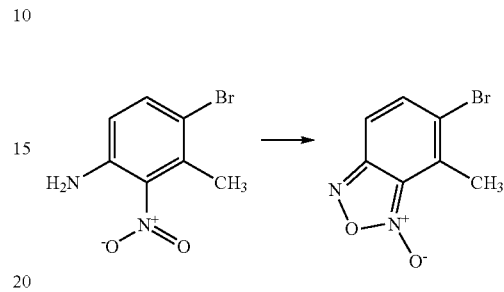

4-bromo-3-methyl-2-nitroaniline (8.2 g, 36 mmol) was stirred in 150 mL ethanol, treated with potassium hydroxide solution (4.4 g, 45 wt. %, 36 mmol) to produce an orange solution. After cooling to 0-5° C., this solution was treated dropwise with commercial bleach solution (100 g, 5 wt. %, 67 mmol) over 30 min to produce a tan slurry. The cooling bath was removed and the mixture was stirred for 30 min more, treated with 600 mL water and the solid product was collected by filtration and washed well with water. The wet solid was taken up in 350 mL ethyl acetate and 150 mL water and filtered to remove a small amount of orange solids. The organic phase was washed with 75 mL saturated NaCl, dried (Na$_2$SO$_4$) and evaporated to give the title compound which was carried on to the deoxygenation step without further purification (7 g, 85%): EIMS m/z 228.

Preparation 42:
5-Bromo-4-methylbenzo[c][1,2,5]oxadiazole

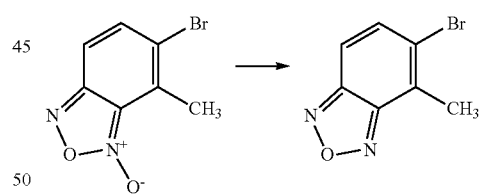

The crude 6-bromo-7-methylbenzo[c][1,2,5]oxadiazole 1-oxide (7.0 g, 31 mmol) from the above step was slurried in 100 ml ethanol, treated with triethyl phosphite (6.2 g, 37 mmol) and heated to reflux for 20 h. The volatiles were removed by rotary evaporation, the residue taken up in 100 mL dichloromethane and stirred with 50 mL 5% bleach solution for 20 min. The organic phase was washed with 20 mL saturated NaCl, dried (Na$_2$SO$_4$) and evaporated. The material was purified by flash chromatography with 0-30% ethyl acetate-hexane gradient to give the title compound as an orange solid (3.6 g, 55%): mp 80-83° C.; $^1$H NMR (400 MHz, Chloroform-d) δ 7.56 (d, J=9.3, 1H), 7.50 (d, J=9.4 Hz, 1H), 2.71 (s, 3H). EIMS m/z 212.

Preparation 43: 4-Bromobenzo[c][1,2,5]oxadiazole

2-Bromo-6-fluoroaniline (7.3 g, 38.4 mmol) was dissolved in dichloromethane (180 mL), cooled to 0-5° C. and treated with a solution of the 3-chlorobenzoperoxoic acid (18.94 g, 77 mmol) in dichloromethane (200 mL) over ca 90 min. After completion of the addition, the reaction mixture was allowed to warm up and stir for 2 h. The reaction mixture was diluted with additional dichloromethane and agitated with 2% $Na_2SO_3$ solution, saturated $NaHCO_3$, dried, and evaporated. The solid residue was slurried with hexane (200 mL) and collected by filtration, washed with hexane and sucked dry to give 4.4 g of the nitroso compound as a white solid. The GC-MS looks like the starting aniline (m/z=190/193) but the aniline is a liquid. The crude nitroso compound was stirred in dry DMSO (50 mL) to produce a pale green slurry. Sodium azide (2.498 g, 38.4 mmol) was added in portions over 30 min with cooling applied to keep the temperature less than 30° C. GCMS showed formation of the oxadiazole (m/z=198/200). The mixture was stirred overnight, partitioned between ethyl acetate and water to produce a clear organic phase and a nearly clear aqueous phase. The organic phase was washed with water, washed with saturated NaCl, dried and evaporated to give the title compound as a white solid (4.0 g, 50%): mp 106-108° C.; $^1$H NMR (400 MHz, $CDCl_3$) δ 7.82 (d, J=9.0 Hz, 1H), 7.65 (d, J=6.8 Hz, 1H), 7.31 (dd, J=9.0, 6.9 Hz, 1H).

Preparation 44: 5-(4,4,5,5-Tetramethyl-1,3,2-dioxaborolan-2-yl)benzo[c][1,2,5]thiadiazole

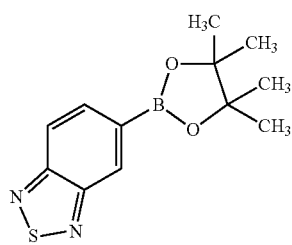 [SMILES: CC1(C)OB(c2ccc3nsnc3c2)OC1(C)C]

Dichloro[1,1'-bis(diphenylphosphino)ferrocene]-palladium(II) (100 mg, 0.14 mmol, 0.03), potassium acetate (1.4 g, 14 mmol), and diboron bis(pinocol) ester (1.2 g, 4.7 mmol) were sequentially added to a stirred solution of 5-bromobenzo[c][1,2,5]thiadiazole (1.0 g, 4.7 mmol) in N,N-dimethylformamide (12 mL) at 23° C. The resulting dark brown mixture was sealed under nitrogen, heated to 80° C., and stirred for 24 h. The cooled reaction mixture was diluted with water (500 mL) and extracted with diethyl ether (4×100 mL). The combined organic layers were diluted with hexane (100 mL) and washed with water (1×200 mL). The organic layer was dried (magnesium sulfate), gravity filtered, and concentrated by rotary evaporation to afford the title compound as a brown powder (960 mg, 80% yield): IR (KBr thin film) 2977 (m), 2930 (w), 1607 (w), 1471 (m) cm$^{-1}$; $^1$H NMR (400 MHz, $CDCl_3$) δ 8.54 (s, 1H), 7.93-8.01 (m, 2H), 1.40 (s, 12H).

Another compound prepared by the method described in preparation 44 was:

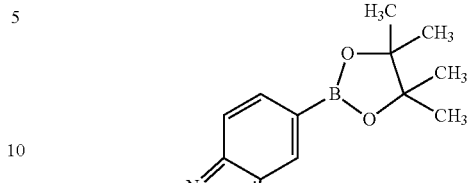

5-(4,4,5,5-Tetramethyl-1,3,2-dioxaborolan-2yl)benzo[c][1,2,5]oxadiazole (the purity was estimated to be ~60%).

Preparation 45: 5-Fluoro-6-(4,4,5,5-tetramethyl-1,3,2-dioxaborolan-2-yl)benzo[c][1,2,5]oxadiazole

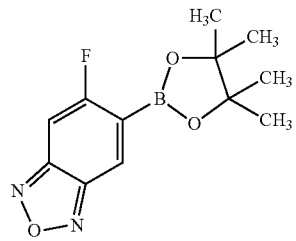 [SMILES: CC1(C)OB(c2cc3nonc3cc2F)OC1(C)C]

5-Bromo-6-fluorobenzo[c][1,2,5]oxadiazole (1.0 g, 4.61 mmol), $PdCl_2$(dppf)-$CH_2Cl_2$Adduct (0.376 g, 0.461 mmol), potassium acetate (0.905 g, 9.22 mmol), and bis(pinacolato) diboron (1.229 g, 4.84 mmol) were combined in 10 mL dry dioxane, sparged with a stream of $N_2$ for 10 min and warmed to 75° C. After 1 h GC-MS showed complete conversion of the bromide into the boronate (m/z=264). After 90 min total heating the mixture was cooled, shaken with ethyl acetate and water. The organic phase was washed with saturated NaCl, dried and evaporated to give a dark oil. This material was stirred with 10 mL hexane for 15 min which caused a brown precipitate to form. This material was removed by filtration and the filtrate was evaporated to give 1.6 g of the boronate as a brown oil of an estimated 80% purity: $^1$HMR (400 MHz, $CDCl_3$) δ 8.38 (d, J=4.9 Hz, 1H), 7.36 (dd, J=8.4, 0.7 Hz, 1H), 1.40 (s, 1H), 1.40 (s, 1H). $^{19}$F NMR (376 MHz, CDCl3) δ -97.20.

EXAMPLES OF SYNTHESIS OF COMPOUNDS OF FORMULA (I)

Example 1

Methyl 4-amino-6-(benzo[c][1,2,5]oxadiazol-5-yl)-3-chloro-5-fluoropicolinate

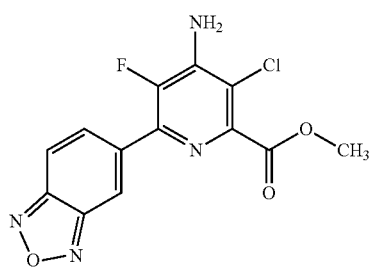

Bis(triphenylphosphine)palladium(II) chloride (110 mg, 0.16 mmol) and sodium carbonate (210 mg, 2.0 mmol) were sequentially added to a stirred mixture of ~60% 5-(4,4,5,5-tetramethyl-1,3,2-dioxaborolan-2-yl)benzo[c][1,2,5]oxadiazole (900 mg, 2.2 mmol) and methyl 4-amino-3,6-dichloro-5-fluoropicolinate (480 mg, 2.0 mmol, 1.0 equiv) in a 1:1 mixture of water:acetonitrile (6.8 mL) at 23° C. The resulting brown mixture was heated to 85° C. and stirred for 4 h. The cooled reaction mixture was diluted with water (150 mL) and extracted with dichloromethane (3×80 mL). The combined organic layers were dried (magnesium sulfate), gravity filtered, and concentrated by rotary evaporation. The residue was purified by reverse phase column chromatography (5% acetonitrile to 100% acetonitrile gradient) to afford the title compound as a tan powder (370 mg, 57% yield).

The preparation method used in this example is referred to in Table 2 as "Coupling 1."

Example 2

Methyl 6-amino-2-(6-fluorobenzo[c][1,2,5]oxadiazol-5-yl)-5-methoxypyrimidine-4-carboxylate

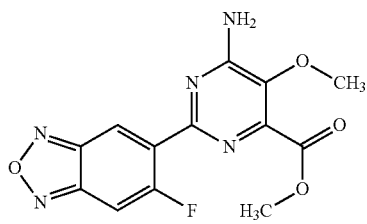

Methyl 6-amino-2-chloro-5-methoxypyrimidine-4-carboxylate (400 mg, 1.838 mmol), 5-fluoro-6-(4,4,5,5-tetramethyl-1,3,2-dioxaborolan-2-yl)benzo[c][1,2,5]oxadiazole (789 mg, 2.390 mmol), bis(triphenylphosphine)palladium(II) chloride (129 mg, 0.184 mmol), and cesium fluoride (558 mg, 3.68 mmol) were combined in 4 mL 1:1 ACN-water and heated at 115° C. for 30 min in a microwave reactor. The cooled reaction mixture was partitioned between ethyl acetate and water. The organic phase was washed with saturated NaCl, dried, and evaporated. The product was purified by flash chromatography (SiO$_2$, eluting with 5-30% ethyl acetate in dichloromethane) to provide the title compound (240 mg, 39%).

The preparation method used in this example is referred to in Table 2 as "Coupling 2."

Example 3

Methyl 4-amino-3-chloro-6-(6-fluorobenzo[c][1,2,5]oxadiazol-5-yl)picolinate (Compound 4)

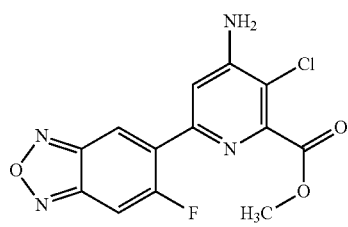 [SMILES: COC(=O)c1nc(-c2cc3nonc3cc2F)cc(N)c1Cl]

5-bromo-6-fluorobenzo[c][1,2,5]oxadiazole (300 mg, 1.383 mmol) was dissolved in 7 ml dry DMF and the solution was sparged with a stream of nitrogen for 10 min. Bis(triphenylphosphine)palladium(II) chloride (97 mg, 0.138 mmol), copper(I) iodide (26.3 mg, 0.138 mmol) and methyl 4-acetamido-3-chloro-6-(trimethylstannyl)picolinate (541 mg, 1.383 mmol) were added and the mix was heated at 70° C. for 3 h. The reaction mixture was cooled and partitioned between ethyl acetate and water. The organic phase was washed with saturated NaCl, dried, and evaporated. The residue was purified by flash chromatography (SiO$_2$, eluting with 0-30% ethyl acetate in dichloromethane) to provide the intermediate amide as a white solid (220 mg, 44%): $^1$H NMR (400 MHz, CDCl$_3$) δ 9.05 (d, J=2.3 Hz, 1H), 8.43 (dd, J=6.8, 0.6 Hz, 1H), 8.04 (s, 1H), 7.56 (dd, J=9.7, 0.6 Hz, 1H), 4.05 (s, 3H), 2.36 (s, 3H). $^{19}$F NMR (376 MHz, CDCl$_3$) δ −105.80. The amide was dissolved in methanol (20 mL), treated with acetyl chloride (2 mL) and heated at reflux for 1 h. The reaction mixture was concentrated under vacuum and the residue partitioned between ethyl acetate and water. The pH was adjusted to 7 with saturated NaHCO$_3$. The organic phase was washed with saturated NaCl, dried, and evaporated to provide the title compound (185 mg, 41.5%).

The preparation method used in this example is referred to in Table 2 as "Coupling 3."

Example 4

Methyl 4-amino-3-chloro-5-fluoro-6-(6-fluorobenzo[c][1,2,5]oxadiazol-5-yl)picolinate (Compound 3)

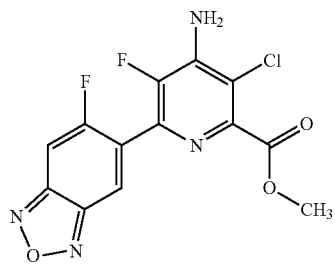 [SMILES: COC(=O)c1nc(-c2cc3nonc3cc2F)c(F)c(N)c1Cl]

Methyl 4-amino-3-chloro-5-fluoro-6-(trimethylstannyl)picolinate (320 mg, 0.86 mmol) and 5-bromo-6-fluorobenzo[c][1,2,5]oxadiazole (170 mg, 0.78 mmol) were combined in 5 mL dry N,N-dimethylformamide, deaerated with a stream of nitrogen for 15 min. Bis(triphenylphosphine)palladium(II) chloride (55 mg, 0.078 mmol) and cuprous iodide (15 mg, 0.078 mmol) were added and the mixture was heated to 70° C. for 4 h. The mixture was shaken with 20 mL ethyl acetate, 10 mL saturated NaCl, dried (Na$_2$SO$_4$) and the residue was chromatographed on silica with a 5-30% ethyl acetate-hexane gradient to give 50 mg of the title compound as a white solid (50 mg, 19%): mp 180-182° C.; $^1$H NMR (400 MHz, CDCl$_3$) δ 8.16 (dd, J=6.2, 0.5 Hz, 1H), 7.54 (dd, J=8.7, 0.5 Hz, 1H), 5.07 (s, 2H), 4.00 (s, 3H); $^{19}$F NMR (376 MHz, CDCl$_3$) δ −105.64, −105.72, −137.68, −137.76; ESIMS m/z 341 ([M+H]$^+$), 339 ([M−H]$^−$).

The preparation method used in this example is referred to in Table 2 as "Coupling 4."

Example 5

Methyl 4-amino-3-chloro-6-(4-methoxybenzo[c][1,2,5]oxadiazol-5-yl)picolinate (Compound 9)

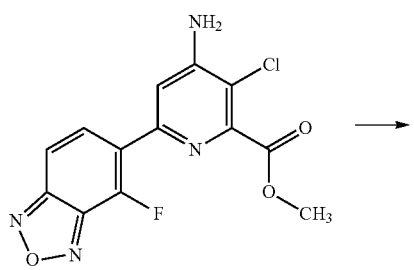

↓

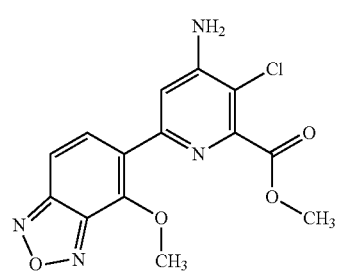

Methyl 4-amino-3-chloro-6-(4-fluorobenzo[c][1,2,5]oxadiazol-5-yl)picolinate (70 mg, 0.21 mmol) was dissolved in 2 mL dry methanol, treated with 0.20 mL 30% sodium methoxide solution in methanol and stirred for 90 min at 20° C. The excess sodium methoxide was neutralized by addition of acetic acid and the volatiles were removed by rotary evaporation. The residue was taken up in 10 mL ethyl acetate, washed with 2 mL saturated NaHCO$_3$, 2 mL saturated NaCl, dried (Na$_2$SO$_4$) and evaporated to give the title compound as white solid (51 mg, 72%): mp 142-144° C.; $^1$H NMR (400 MHz, CDCl$_3$) δ 8.01 (d, J=9.3 Hz, 1H), 7.51 (d, J=9.3 Hz, 1H), 7.44 (s, 1H), 4.86 (s, 2H), 4.39 (s, 3H), 4.00 (s, 3H); ESIMS m/z 335 ([M+H]$^+$), 333 ([M–H]$^-$).

Example 6

4-Amino-3-chloro-6-(6-methoxybenzo[c][1,2,5]oxadiazol-5-yl)picolinic acid (Compound 5)

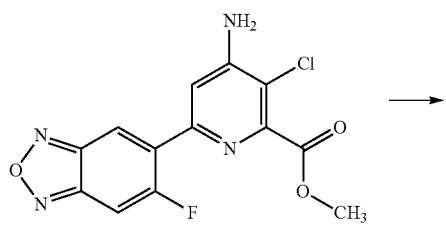

↓

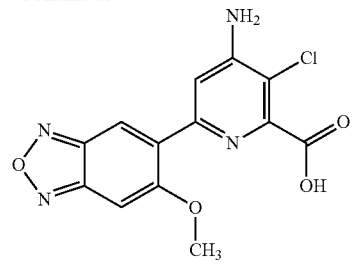

4-Amino-3-chloro-6-(6-fluorobenzo[c][1,2,5]oxadiazol-5-yl)picolinate (280 mg, 0.87 mmol) was dissolved in 30 mL dry methanol, treated with sodium hydroxide (3.0 mL, 2 M, 6.0 mmol) and stirred at 20° C. for 2 h. The volatiles were removed under vacuum, the residue dissolved in 30 mL water and the pH adjusted to 2.5 by addition of 1 M HCl. The precipitate was collected by filtration washed with water and dried under vacuum at 80° C. to give 250 mg of impure product. This material was treated a solution of sodium methoxide prepared from sodium (120 mg, 5.2 mmol) in 10 mL dry methanol and heated at reflux for 2 h. After cooling the volatiles were removed by rotary evaporation, the solid acid was isolated as above and dried to give the title compound as a white solid (250 mg, 90%). mp 178-180° C. $^1$H NMR (400 MHz, DMSO-d$_6$) δ 13.55 (s, 1H), 8.12 (s, 1H), 7.39 (s, 1H), 7.09 (s, 1H), 6.80 (s, 2H), 3.95 (s, 3H); ESIMS m/z 321 ([M+H]$^+$), 319 ([M–H]$^-$).

Example 7

4-Amino-6-(benzo[c][1,2,5]oxadiazol-5-yl)-3-chloro-5-fluoropicolinic acid (Compound 2)

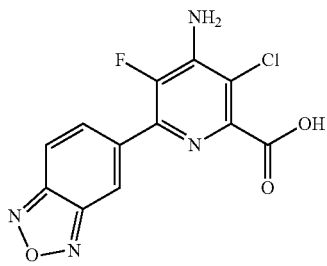 [SMILES: Nc1c(F)c(-c2ccc3nonc3c2)nc(C(=O)O)c1Cl]

A 2M solution of aqueous sodium hydroxide (620 microliters (μL), 1.2 mmol) was added to a stirred suspension of methyl 4-amino-6-(benzo[c][1,2,5]oxadiazol-5-yl)-3-chloro-5-fluoropicolinate (200 mg, 0.62 mmol) in methanol (1.3 mL) at 23° C. The heterogeneous light brown mixture was stirred at 23° C. for 72 h. The reaction mixture was adjusted to approximately pH=4 via dropwise addition of concentrated hydrochloric acid and concentrated via rotary evaporation. The residue was slurried in water and vacuum filtered to afford the title compound (120 mg, 63% yield).

The preparation method used in this example is referred to in Table 2 as "Hydrolysis."

TABLE 2

Compound Number, Structure, Preparation and Appearance

| Compound No. | Structure | Appearance | Prepared as described in Example: | Pre-Cursor(s) |
|---|---|---|---|---|
| 1 | 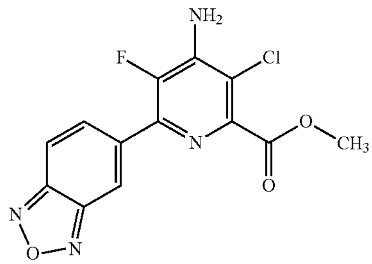 | Tan Powder | Coupling 1 | Head B; 5-(4,4,5,5-tetramethyl-1,3,2-dioxaborolan-2-yl)benzo[c][1,2,5]oxadiazole |
| 2 | 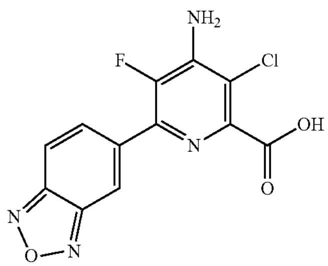 [SMILES: Nc1c(F)c(-c2ccc3nonc3c2)nc(C(=O)O)c1Cl] | Light Brown Powder | Hydrolysis | Compound 1 |
| 3 | 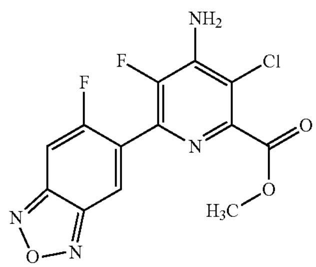 [SMILES: COC(=O)c1nc(-c2cc3nonc3cc2F)c(F)c(N)c1Cl] | White Solid | Coupling 4 | Head J; 5-bromo-6-fluorobenzo[c][1,2,5]oxadiazole |
| 4 | 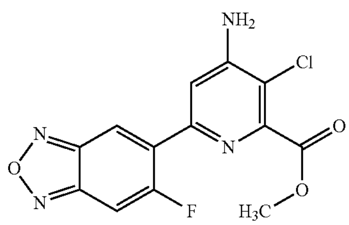 [SMILES: COC(=O)c1nc(-c2cc3nonc3cc2F)cc(N)c1Cl] | White Solid | Coupling 3 | Head K; 5-bromo-6-fluorobenzo[c][1,2,5]oxadiazole |
| 5 | 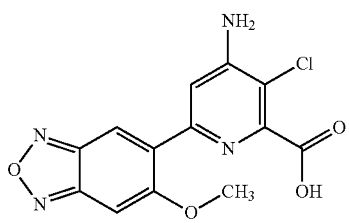 [SMILES: COc1cc2nonc2cc1-c1cc(N)c(Cl)c(C(=O)O)n1] | White Solid | 6 | As described |
| 6 | 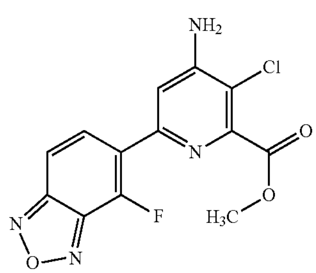 [SMILES: COC(=O)c1nc(-c2ccc3nonc3c2F)cc(N)c1Cl] | White Solid | Coupling 3 | Head K; 5-bromo-4-fluorobenzo[c][1,2,5]oxadiazole |

TABLE 2-continued

Compound Number, Structure, Preparation and Appearance

| Compound No. | Structure | Appearance | Prepared as described in Example: | Pre-Cursor(s) |
|---|---|---|---|---|
| 7 | 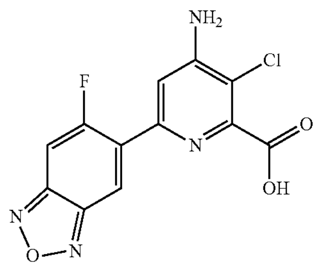 [SMILES: Nc1cc(-c2cc3nonc3cc2F)nc(C(=O)O)c1Cl] | White Solid | Hydrolysis | Compound 4 |
| 8 | 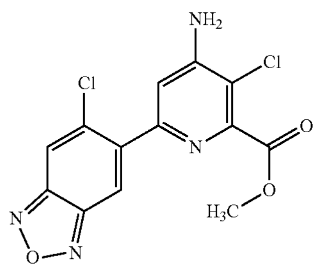 [SMILES: COC(=O)c1nc(-c2cc3nonc3cc2Cl)cc(N)c1Cl] | White Solid | Coupling 3 | Head K; 5-bromo-6-chlorobenzo[c][1,2,5]oxadiazole |
| 9 | 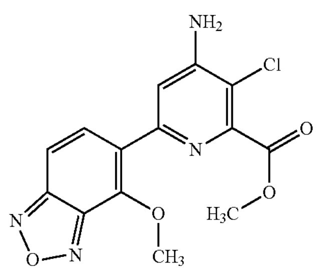 [SMILES: COC(=O)c1nc(-c2ccc3nonc3c2OC)cc(N)c1Cl] | White Solid | 5 | As described |
| 10 | 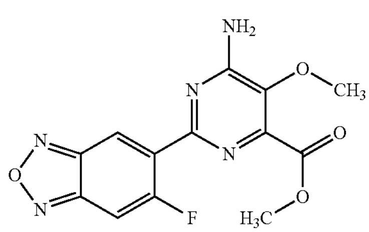 [SMILES: COC(=O)c1nc(-c2cc3nonc3cc2F)nc(N)c1OC] | Tan Solid | Coupling 2 | Head C; 5-fluoro-6-(4,4,5,5-tetramethyl-1,3,2-dioxaborolan-2-yl)benzo[c][1,2,5]oxadiazole |
| 11 | 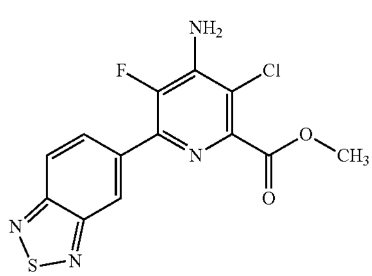 [SMILES: COC(=O)c1nc(-c2ccc3nsnc3c2)c(F)c(N)c1Cl] | Tan Powder | Coupling 1 | Head B; 5-(4,4,5,5-tetramethyl-1,3,2-dioxaborolan-2-yl)benzo[c][1,2,5]thiadiazole |

TABLE 2-continued

Compound Number, Structure, Preparation and Appearance

| Compound No. | Structure | Appearance | Prepared as described in Example: | Pre-Cursor(s) |
|---|---|---|---|---|
| 12 | 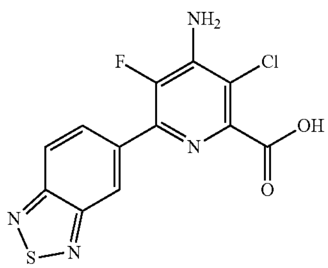 | Off-White Powder | Hydrolysis | Compound 11 |
| 13 | 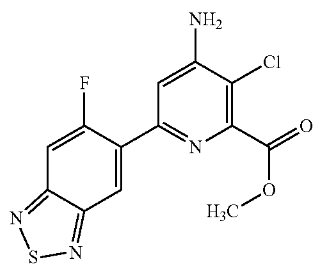 [SMILES: COC(=O)c1nc(-c2cc3nsnc3cc2F)cc(N)c1Cl] | White Solid | Coupling 3 | Head K; 5-bromo-6-fluorobenzo[c][1,2,5]thiadiazole |
| 14 | 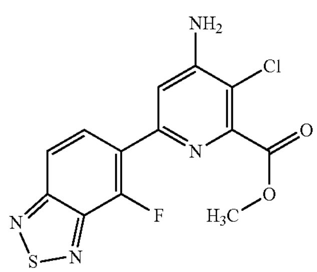 [SMILES: COC(=O)c1nc(-c2ccc3nsnc3c2F)cc(N)c1Cl] | Tan Solid | Coupling 3 | Head K; 5-bromo-4-fluorobenzo[c][1,2,5]thiadiazole |
| 15 | 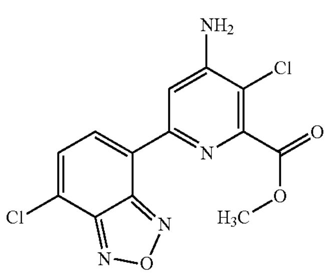 [SMILES: COC(=O)c1nc(-c2ccc(Cl)c3nonc23)cc(N)c1Cl] | Tan Solid | Coupling 3 | Head K; 4-bromo-7-chlorobenzo[c][1,2,5]oxadiazole |
| 16 | 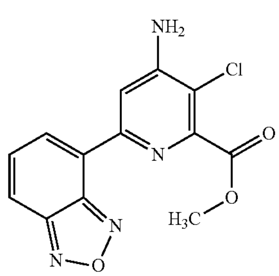 [SMILES: COC(=O)c1nc(-c2cccc3nonc23)cc(N)c1Cl] | Yellow Solid | Coupling 3 | Head K; 4-Bromobenzo[c][1,2,5]oxadiazole |

TABLE 2-continued

Compound Number, Structure, Preparation and Appearance

| Compound No. | Structure | Appearance | Prepared as described in Example: | Pre-Cursor(s) |
|---|---|---|---|---|
| 17 | (structure: 4-amino-3-chloro-6-(7-methylbenzo[c][1,2,5]oxadiazol-5-yl)picolinic acid methyl ester) | White Solid | Coupling 3 | Head K; 5-Bromo-4-methylbenzo[c][1,2,5]oxadiazole |
| 18 | (structure: 4-amino-3-chloro-6-(7-chlorobenzo[c][1,2,5]oxadiazol-5-yl)picolinic acid methyl ester) | White Solid | Coupling 3 | Head K; 5-bromo-4-chlorobenzo[c][1,2,5]oxadiazole |

TABLE 3

Analytical Data for Compounds in Table 1

| Compound No. | MP (° C.) | HNMR |
|---|---|---|
| 1 | 180-182 | $^1$H NMR (400 MHz, CDCl$_3$) δ 8.44 (br s, 1H), 8.14 (dt, J = 10, 1 Hz, 1H), 7.94 (dd, J = 10, 1 Hz, 1H), 5.02 (br s, 2H), 4.01 (s, 3H) |
| 2 | 192-197 (dec) | $^1$H NMR (400 MHz, DMSO-d$_6$) δ 8.45 (s, 1H), 8.21 (d, J = 10 Hz, 1H), 8.13 (d, J = 10 Hz, 1H), 6.86 (br s, 2H) |
| 3 | 180-182 | $^1$H NMR (400 MHz, CDCl$_3$) δ 8.16 (dd, J = 6.2, 0.5 Hz, 1H), 7.54 (dd, J = 8.7, 0.5 Hz, 1H), 5.07 (s, 2H), 4.00 (s, 3H). |
| 4 | 199-201 | $^1$H NMR (400 MHz, CDCl$_3$) δ 8.47 (d, J = 6.8 Hz, 1H), 7.53 (dd, J = 10.0, 0.5 Hz, 1H), 7.17 (d, J = 2.6 Hz, 1H), 4.96 (s, 2H), 4.03 (s, 3H). |
| 5 | 198-199 | $^1$H NMR (400 MHz, DMSO-d$_6$) δ 13.55 (s, 1H), 8.12 (s, 1H), 7.39 (s, 1H), 7.09 (s, 1H), 6.80 (s, 2H), 3.95 (s, 3H). |
| 6 | 175-177 | $^1$H NMR (400 MHz, DMSO-d$_6$) δ 8.08 (dd, J = 9.4, 6.6 Hz, 1H), 7.98 (d, J = 9.4 Hz, 1H), 7.46 (d, J = 1.5 Hz, 1H), 7.05 (s, 2H), 3.91 (s, 3H). |
| 7 | 177-178 | $^1$H NMR (400 MHz, DMSO-d$_6$) δ 13.75 (s, 1H), 8.45 (d, J = 6.9 Hz, 1H), 8.11 (d, J = 10.5 Hz, 1H), 7.16 (d, J = 2.0 Hz, 1H), 6.88 (s, 2H). |
| 8 | 224-226 | $^1$H NMR (400 MHz, CDCl$_3$) δ 8.04 (d, J = 0.7 Hz, 1H), 8.01 (d, J = 0.7 Hz, 1H), 6.96 (s, 1H), 4.95 (s, 2H), 4.00 (s, 3H). |
| 9 | 142-144 | $^1$H NMR (400 MHz, CDCl$_3$) δ 8.01 (d, J = 9.3 Hz, 1H), 7.51 (d, J = 9.3 Hz, 1H), 7.44 (s, 1H), 4.86 (s, 2H), 4.39 (s, 3H), 4.00 (s, 3H). |
| 10 | 183-185 | $^1$H NMR (400 MHz, CDCl$_3$) δ 8.38 (dd, J = 6.7, 0.7 Hz, 1H), 7.50 (dd, J = 9.3, 0.7 Hz, 1H), 5.50 (s, 2H), 4.02 (s, 3H), 3.99 (s, 3H). |
| 11 | 196-198 | $^1$H NMR (400 MHz, CDCl$_3$) δ 8.60 (br s, 1H), 8.28 (dt, J = 9.5, 1.5 Hz, 1H), 8.09 (dd, J = 9.5, 1 Hz, 1H), 5.00 (br s, 2H), 4.02 (s, 3H) |
| 13 | 218-220 | $^1$H NMR (400 MHz, CDCl$_3$) δ 8.61 (d, J = 7.5 Hz, 1H), 7.72 (d, J = 11.2 Hz, 1H), 7.25 (d, J = 2.4 Hz, 1H), 4.92 (s, 2H), 4.03 (s, 3H). |
| 14 | | $^1$H NMR (400 MHz, CDCl$_3$) δ 8.39 (dd, J = 9.3, 7.3 Hz, 1H), 7.86 (d, J = 9.3 Hz, 1H), 7.46 (d, J = 1.3 Hz, 1H), 4.93 (s, 2H), 4.03 (s, 3H). |
| 15 | | $^1$H NMR (400 MHz, CDCl$_3$) δ 8.46 (d, J = 7.6 Hz, 1H), 8.08 (s, 1H), 7.55 (d, J = 7.6 Hz, 1H), 5.01 (s, 2H), 4.04 (s, 3H). |
| 16 | 157-160 | $^1$H NMR (400 MHz, CDCl$_3$) δ 8.50 (d, J = 6.9 Hz, 1H), 8.14 (s, 1H), 7.88 (d, J = 9.0 Hz, 1H), 7.56 (dd, J = 9.0, 6.9 Hz, 1H), 5.00 (s, 2H), 4.04 (s, 3H) |
| 17 | 182-185 | $^1$H NMR (400 MHz, CDCl$_3$) δ 7.69 (dd, J = 9.3, 0.4 Hz, 1H), 7.53 (d, J = 9.3 Hz, 1H), 6.85 (s, 1H), 4.94 (s, 2H), 4.00 (s, 3H), 2.67 (s, 3H). |
| 18 | | $^1$H NMR (400 MHz, CDCl$_3$) δ 7.80 (d, J = 2.4 Hz, 1H), 7.26 (d, J = 3.0 Hz, 2H), 4.98 (s, 2H), 4.01 (s, 3H). |

TABLE 4

Percent Control Rating Conversion Table

| Rating | % Control |
|---|---|
| A | 95-100 |
| B | 85-94 |
| C | 75-84 |
| D | 60-74 |
| E | 45-59 |
| F | 30-44 |
| G | 0-29 |

Example A

Evaluation of Postemergent Herbicidal Activity

Post-Emergent Test I: Seeds test species were obtained from commercial suppliers and planted into a 5"-round pot containing soil-less media mix (Metro-Mix 360®, Sun Gro Horticulture). Postemergence treatments were planted 8-12 days (d) prior to application and cultured in a greenhouse equipped with supplemental light sources to provide a 16 hour (h) photoperiod at 24-29° C. All pots were surface irrigated.

Approximately 10 milligrams (mg) of each compound were dissolved in 1.3 mL acetone-DMSO (97:3, v/v) and diluted with 4.1 mL water-isopropanol-crop oil concentrate (78:20:2, v/v/v) containing 0.02% Triton X-155. Treatments were serial diluted with the above formulation solvent to provide 1.85, 0.926, 0.462 and 0.231 mg/mL of test compound delivered in 2.7 mL/pot (roughly equivalent to 4.0, 2.0, 1.0, and 0.5 kg/ha, respectively).

Formulated compounds were applied using a DeVilbiss® compressed air sprayer at 2-4 pounds per square inch (psi). Following treatment, pots were returned to the greenhouse for the duration of the experiment. All pots were sub-irrigated as need to provide optimum growing conditions. All pots were fertilized one time per week by subirrigating with Peters Peat-Lite Special® fertilizer (20-10-20).

Phytotoxicity ratings were obtained 10 days after treatment postemergence applications. All evaluations were made visually on a scale of 0 to 100 where 0 represents no activity and 100 represents complete plant death. Visual assessments of plant injury were made based on growth reduction, discoloration, leaf deformity and necrosis.

Some of the compounds tested, application rates employed, plant species tested, and results are given in Table 5.

TABLE 5

Post-emergent Test I Herbicidal Activity on Key Broadleaf and Grass Weed as well as Crop Species

| Compound Number | Application Rate (Kg ai/ha) | Visual Growth Reduction (%) 10 Days After Application | | | | |
|---|---|---|---|---|---|---|
| | | AVEFA | ECHCG | HELAN | IPOHE | SETFA |
| 6 | 4 | G | G | G | G | G |
| 10 | 4 | C | C | C | C | C |

The following abbreviations are used in Table 5:
AVEFA: wild oats (*Avena fatua*)
ECHCG: barnyardgrass (*Echinochloa crus-galli*)
HELAN: sunflower (*Helianthus annuus*)
IPOHE: ivyleaf morningglory (*Ipomoea hederecea*)
SETFA: giant foxtail (*Setaria faberi*)
g ai/ha: grams active ingredient per hectare

Example B

Evaluation of Postemergent Herbicidal Activity

Post-Emergent Test II: Seeds or nutlets of the desired test plant species were planted in Sun Gro Metro-Mix® 360 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7-21 d in a greenhouse with an approximate 15 h photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 25 mL glass vial and was dissolved in 4 mL of a 97:3 v/v mixture of acetone and DMSO to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of 97:3 v/v mixture of acetone and DMSO and 10 mL of an aqueous mixture containing acetone, water, isopropyl alcohol, DMSO, Atplus 411F crop oil concentrate, and Triton X®-155 surfactant in a 48.5:39:10:1.5:1.0:0.02 v/v ratio to obtain ½×, ¼×, ⅛× and ¹⁄₁₆× rates of the high rate. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by subirrigation to prevent wash-off of the test compounds. After 14 d, the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Tables 6 and 7.

TABLE 6

Post-emergent Test II Herbicidal Activity on Key Broadleaf Weed and Crop Species

| C. No. | Application Rate (g ai/ha) | Visual Growth Reduction (%) 14 Days After Application | | | | | |
|---|---|---|---|---|---|---|---|
| | | ABUTH | AMARE | BRSNN | CHEAL | EPHHL | HELAN |
| 1 | 35 | B | C | D | A | D | B |
| | 70 | B | C | D | A | D | A |
| | 140 | A | A | D | A | D | A |

TABLE 6-continued

Post-emergent Test II Herbicidal Activity on Key Broadleaf Weed and Crop Species

| C. No. | Application Rate (g ai/ha) | Visual Growth Reduction (%) 14 Days After Application | | | | | |
|---|---|---|---|---|---|---|---|
| | | ABUTH | AMARE | BRSNN | CHEAL | EPHHL | HELAN |
| 2 | 35 | C | A | D | A | D | B |
| | 70 | C | A | C | A | D | B |
| | 140 | B | A | C | A | D | A |
| 3 | 35 | E | A | B | B | E | B |
| | 70 | G | A | B | B | E | B |
| | 140 | G | A | A | B | D | A |
| 4 | 35 | B | A | B | B | A | B |
| | 70 | A | A | A | A | A | B |
| | 140 | A | A | A | A | A | B |
| 5 | 35 | G | n/a | G | G | G | G |
| | 70 | G | n/a | G | G | G | G |
| | 140 | G | n/a | G | G | G | G |
| 8 | 35 | G | G | G | G | G | G |
| | 70 | G | G | G | G | G | G |
| | 140 | G | G | F | G | G | G |
| 9 | 35 | G | E | G | D | G | G |
| | 70 | G | D | G | D | G | G |
| | 140 | G | D | G | C | G | G |
| 10 | 35 | G | n/a | D | G | E | G |
| | 70 | G | n/a | C | G | D | G |
| | 140 | G | n/a | C | G | C | n/a |
| 11 | 35 | B | A | D | B | A | B |
| | 70 | A | A | C | A | A | B |
| | 140 | A | A | C | A | A | A |
| | 280 | n/a | n/a | n/a | n/a | n/a | n/a |
| 12 | 35 | B | A | C | B | A | A |
| | 70 | B | A | C | A | A | A |
| | 140 | B | A | C | A | A | A |
| | 280 | n/a | n/a | n/a | n/a | n/a | n/a |
| 13 | 35 | C | A | A | B | A | F |
| | 70 | B | A | A | A | A | D |
| | 140 | B | A | A | A | A | C |
| 14 | 35 | G | F | G | E | D | G |
| | 70 | G | F | G | D | B | G |
| | 140 | G | E | G | C | A | F |
| 16 | 35 | G | B | F | D | G | G |
| | 70 | G | A | E | C | G | F |
| | 140 | G | A | D | B | G | D |
| 17 | 35 | G | A | D | B | G | G |
| | 70 | E | A | C | A | G | E |
| | 140 | D | A | B | A | G | D |
| 18 | 35 | G | A | D | C | G | G |
| | 70 | G | A | C | B | G | F |
| | 140 | G | A | C | A | F | D |

The following abbreviations are used in Table 6:
ABUTH: velvetleaf (*Abutilon theophrasti*)
AMARE: redroot pigweed (*Amaranthus retroflexus*)
BRSNN: oilseed rape, canola (*Brassica napus*)
CHEAL: lambsquarters (*Chenopodium album*)
EPHHL: wild poinsettia (*Euphorbia heterophylla*)
HELAN: sunflower (*Helianthus annuus*)
g ai/ha: grams active ingredient per hectare

TABLE 7

Post-emergent Test II Herbicidal Activity on Key Grass and Sedge Weeds as well as Grass Crops

| C. No. | Application Rate (g ai/ha) | Visual Growth Reduction (%) 14 Days After Application | | | | | |
|---|---|---|---|---|---|---|---|
| | | CYPES | ECHCG | SETFA | ORYSA | TRZAS | ZEAMX |
| 1 | 35 | G | C | n/a | G | E | D |
| | 70 | G | C | n/a | G | E | D |
| | 140 | A | n/a | n/a | G | D | D |

TABLE 7-continued

Post-emergent Test II Herbicidal Activity on Key Grass and Sedge Weeds as well as Grass Crops

| C. No. | Application Rate (g ai/ha) | Visual Growth Reduction (%) 14 Days After Application | | | | | |
|---|---|---|---|---|---|---|---|
| | | CYPES | ECHCG | SETFA | ORYSA | TRZAS | ZEAMX |
| 2 | 35 | G | D | n/a | G | D | D |
| | 70 | G | C | n/a | G | D | D |
| | 140 | G | C | n/a | G | D | D |
| 3 | 35 | D | A | E | G | E | D |
| | 70 | A | A | E | G | E | D |
| | 140 | A | C | E | G | D | C |
| 4 | 35 | A | B | D | G | D | B |
| | 70 | A | A | D | G | C | B |
| | 140 | A | B | D | F | C | B |
| 5 | 35 | G | G | G | G | G | G |
| | 70 | G | G | G | G | G | G |
| | 140 | G | G | G | G | G | G |
| 8 | 35 | G | G | G | G | G | G |
| | 70 | G | G | G | G | G | G |
| | 140 | G | G | G | G | G | G |
| 9 | 35 | G | G | G | G | G | n/a |
| | 70 | G | G | G | G | G | n/a |
| | 140 | G | G | G | G | G | n/a |
| 10 | 35 | G | G | G | G | G | G |
| | 70 | G | G | G | G | G | G |
| | 140 | G | G | G | G | G | G |
| 11 | 35 | A | B | E | G | G | D |
| | 70 | A | A | B | G | G | D |
| | 140 | A | A | B | G | G | C |
| 12 | 35 | G | C | G | G | G | D |
| | 70 | G | C | G | G | G | D |
| | 140 | G | B | C | G | G | C |
| 13 | 35 | G | C | D | G | G | D |
| | 70 | G | B | D | F | G | C |
| | 140 | F | B | B | F | G | B |
| 14 | 35 | G | G | G | G | G | G |
| | 70 | G | G | G | G | G | G |
| | 140 | G | G | G | G | G | G |
| 16 | 35 | G | G | G | G | G | n/a |
| | 70 | G | G | G | G | G | n/a |
| | 140 | G | G | G | G | G | n/a |
| 17 | 35 | D | G | G | G | G | G |
| | 70 | D | G | G | G | G | G |
| | 140 | C | G | G | G | F | G |
| 18 | 35 | G | G | G | G | G | G |
| | 70 | G | G | G | G | G | G |
| | 140 | F | F | G | G | G | G |

The following abbreviations are used in Table 7:
ECHCG: barnyardgrass (*Echinochloa crus-galli*)
CYPES: yellow nutsedge (*Cyperus esculentus*)
ORYSA: rice (*Oryza sativa*)
SETFA: giant foxtail (*Setaria faberi*)
TRZAS: wheat, spring (*Triticum aestivum*)
ZEAMX: maize, corn (*Zea mays*)
g ai/ha: grams active ingredient per hectare Example C Evaluation of Postemergence Herbicidal Activity in Direct Seeded Rice Seeds or nutlets of the desired test plant species were planted in a soil matrix prepared by mixing a loam soil (43 percent silt, 19 percent clay, and 38 percent sand, with a pH of about 8.1 and an organic matter content of about 1.5 percent) and river sand in an 80 to 20 ratio. The soil matrix was contained in plastic pots with a surface area of 139.7 cm$^2$. When required to ensure good germination and healthy plants, a fungicide treatment and/or other chemical or physical treatment was applied. The plants were grown for 10-17 d in a greenhouse with an approximate 14-h photoperiod which was maintained at about 29° C. during the day and 26° C.

during the night. Nutrients and water were added on a regular basis and supplemental lighting was provided with overhead metal halide 1000-Watt lamps as necessary. The plants were employed for testing when they reached the second or third true leaf stage.

A weighed amount, determined by the highest rate to be tested, of each test compound was placed in 25 mL glass vials and dissolved in a volume of 97:3 v/v acetone-DMSO to obtain 12× stock solutions. If the test compound did not dissolve readily, the mixture was warmed and/or sonicated. The concentrated stock solutions were added to the spray solutions so that the final acetone and DMSO concentrations were 16.2% and 0.5%, respectively. Spray solutions were diluted to the appropriate final concentrations with the addition of 10 mL of an aqueous mixture of 1.5% (v/v) Agri-dex crop oil concentrate. The final spray solutions contained 1.25% (v/v) Agri-dex crop oil concentrate. Compound requirements are based upon a 12 mL application volume at a rate of 187 L/ha. Formulated compounds were applied to the plant material with an overhead Mandel track sprayer equipped with 8002E nozzles calibrated to deliver 187 L/ha over an application area of 0.503 square meters (m²) at a spray height of 18 inches (43 cm) above average plant canopy height. Control plants were sprayed in the same manner with the solvent blank.

The treated plants and control plants were placed in a greenhouse as described above and watered by sub-irrigation to prevent wash-off of the test compounds. After 20-22 days, the condition of the test plants, compared with that of the untreated plants, was determined visually and scored on a scale of 0 to 100 percent where 0 corresponds to no injury and 100 corresponds to complete kill.

By applying the well-accepted probit analysis as described by J. Berkson in *Journal of the American Statistical Society*, 48, 565 (1953) and by D. Finney in *"Probit Analysis"* Cambridge University Press (1952), the above data can be used to calculate $GR_{20}$, $GR_{50}$, $GR_{80}$ and $GR_{90}$ values, which are defined as growth reduction factors that correspond to the effective dose of herbicide required to kill or control 20 percent, 50 percent, 80 percent or 90 percent, respectively, of a target plant.

Some of the application rates and ratios employed, plant species tested, and results are given in Table 8. The following abbreviations are used in Table 8:
AESSE: sensitive jointvetch, *Aeschynomene sensitiva*
BRAPP: broadleaf signalgrass, *Brachiaria platyphylla*
CYPDI: small-flower flatsedge, *Cyperus difformis*
CYPES: yellow nutsedge, *Cyperus esculentus*
CYPIR: rice flatsedge, *Cyperus iria*
DIGSA: large crabgrass, *Digitaria sanguinalis*
ECHCG: barnyardgrass, *Echinochloa crus-galli*
ECHCO: junglerice, *Echinochloa colonum*
LEFCH: Chinese sprangletop, *Leptochloa chinensis*
SCPJU: Japanese bulrush, *Scirpus juncoides*
SEBEX: hemp sesbania, *Sesbania exaltata*
ORYSK: *Oryza sativa*
ORYSJ: *Oryza sativa*
g ai/ha: gram active ingredient per hectare

TABLE 8

Activity of Herbicidal Compounds in Direct Seeded Rice

| Compound No. | Application Rate (g/ai/ha) | BRAPP | CYPDI | CYPES | CYPIR | DIGSA | ECHCG | ECHCO | LEFCH | ORYSJ | ORYSK | SCPJU | SEBEX |
|---|---|---|---|---|---|---|---|---|---|---|---|---|---|
| 11 | 17.5 | G | A | D | G | E | E | E | G | G | G | A | C |
|  | 35 | G | A | G | E | E | C | D | G | G | G | A | A |
|  | 70 | E | A | E | F | D | B | C | G | G | G | A | A |
|  | GR20 | — | — | — | — | — | — | — | — | >70 | >70 | — | — |
|  | GR50 | >70 | 6 | >70 | 78 | 11 | 6 | 15 | 114 | — | — | 4 | 4 |
|  | GR80 | >70 | 11 | >70 | 212 | 628 | 37 | 107 | 186 | — | — | 9 | 11 |
|  | GR90 | >70 | 16 | >70 | 357 | 5310 | 98 | 300 | 239 | — | — | 14 | 19 |

What is claimed is:

1. A compound of the Formula (I):

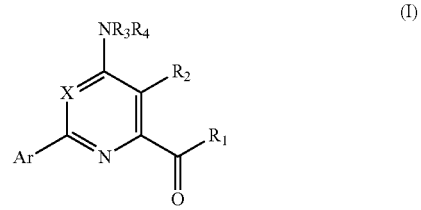

wherein
X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkoxy, $C_1$-$C_3$ alkylthio or $C_1$-$C_3$ haloalkylthio;
$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;
$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;
$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

Ar is one of groups Ar1 to Ar4:

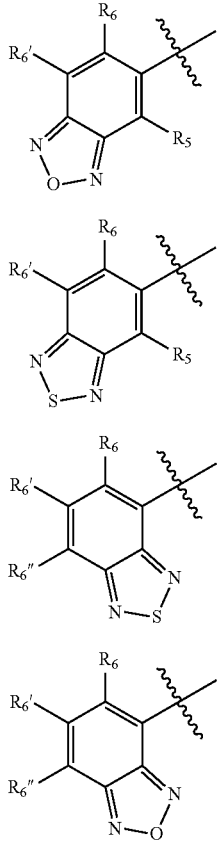

$R^5$, if applicable to the Ar group, is hydrogen, halogen, $C_1$-$C_4$ alkyl, $C_1$-$C_4$ haloalkyl, $C_2$-$C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, or $C_2$-$C_4$ haloalkylamino;

$R^6$ is hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ aminoalkyl or $C_2$-$C_4$ haloaminoalkyl;

$R^{6'}$ is hydrogen or halogen;

$R^{6''}$, if applicable to the Ar group, is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ aminoalkyl or $C_2$-$C_4$ haloaminoalkyl, CN, or $NO_2$;

or an N-oxide or an agriculturally acceptable salt thereof.

2. The compound of claim 1 wherein $R^2$ is halogen, $C_2$-$C_4$-alkenyl, $C_2$-$C_4$ haloalkenyl, or $C_1$-$C_4$-alkoxy.

3. The compound of claim 2 wherein $R^2$ is Cl, methoxy, vinyl, or 1-propenyl.

4. The compound of claim 1 wherein $R^3$ and $R^4$ are both hydrogen.

5. The compound of claim 1 wherein X is N, CH, or CF.

6. The compound of claim 1 wherein Ar is Ar1 or Ar2.

7. The compound of claim 1 wherein Ar is Ar1 or Ar2 and $R^5$ is hydrogen or F.

8. The compound of claim 1 wherein $R^6$ is hydrogen or F.

9. The compound of claim 1 wherein $R^{6'}$ is hydrogen.

10. The compound of claim 1 wherein Ar is Ar3 or Ar4 and $R^{6''}$ is hydrogen or halogen.

11. The compound of claim 1 wherein:
$R^2$ is halogen, $C_2$-$C_4$-alkenyl, $C_2$-$C_4$ haloalkenyl, or $C_1$-$C_4$-alkoxy;
$R^3$ and $R^4$ are hydrogen; and
X is N, CH, or CF.

12. The compound of claim 1 wherein:
$R^2$ is halogen, $C_2$-$C_4$-alkenyl, $C_2$-$C_4$ haloalkenyl, or $C_1$-$C_4$-alkoxy;
$R^3$ and $R^4$ are hydrogen;
X is N, CH, or CF;
Ar is Ar1 or Ar2;
$R^5$ is hydrogen or F; and
$R^6$ is hydrogen.

13. The compound of claim 1 wherein:
$R^2$ is halogen, $C_2$-$C_4$-alkenyl, $C_2$-$C_4$ haloalkenyl, or $C_1$-$C_4$-alkoxy;
$R^3$ and $R^4$ are hydrogen;
X is N, CH, or CF;
Ar is Ar3 or Ar4;
$R^6$ is hydrogen or F;
$R^{6'}$ is hydrogen; and
$R^{6''}$ is hydrogen or halogen.

14. The compound of claim 1 wherein:
$R^2$ is chlorine;
$R^3$ and $R^4$ are hydrogen; and
X is N, CH, or CF.

15. The compound of claim 1 wherein:
$R^2$ is vinyl or 1-propenyl;
$R^3$ and $R^4$ are hydrogen; and
X is N, CH, or CF.

16. The compound of claim 1 wherein:
$R^2$ is methoxy;
$R^3$ and $R^4$ are hydrogen; and
is N, CH, or CF.

17. A herbicidal composition comprising the compound of claim 1 and an agriculturally acceptable adjuvant or carrier.

18. The composition of claim 17, further comprising an additional herbicidal compound.

19. The composition of claim 17, further comprising a safener.

20. A method for controlling undesirable vegetation comprising applying a herbicidally effective amount of a compound of claim 1.

* * * * *